(12) United States Patent
Bowers et al.

(10) Patent No.: US 7,160,953 B2
(45) Date of Patent: *Jan. 9, 2007

(54) POLYMERIC SURFACE COATINGS

(75) Inventors: Roderick William Jonathon Bowers, Norfolk, VA (US); Stephen Alister Jones, Farnham (GB); Peter William Stratford, Farnham (GB)

(73) Assignee: Biocompatibles UK Limited, Farnham (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 196 days.

This patent is subject to a terminal disclaimer.

(21) Appl. No.: 10/795,977

(22) Filed: Mar. 10, 2004

(65) Prior Publication Data

US 2004/0176556 A1    Sep. 9, 2004

Related U.S. Application Data

(60) Continuation of application No. 10/259,468, filed on Sep. 30, 2002, now Pat. No. 6,743,878, which is a continuation of application No. 09/002,861, filed on Jan. 5, 1998, now abandoned, which is a continuation-in-part of application No. 08/475,620, filed on Jun. 7, 1995, now Pat. No. 5,705,583, which is a continuation-in-part of application No. 08/175,348, filed on Mar. 7, 1994, now Pat. No. 5,648,442, which is a division of application No. PCT/GB92/01215, filed on Jul. 6, 1992.

(30) Foreign Application Priority Data

| Jul. 5, 1991 | (GB) | ................... 9114619.1 |
| Aug. 8, 1991 | (GB) | ................... 9117170.2 |
| Apr. 24, 1992 | (GB) | ................... 9208970.5 |

(51) Int. Cl.
*C08F 130/08* (2006.01)

(52) U.S. Cl. .................. 525/326.6; 526/277; 526/279; 526/307; 526/307.1; 526/307.2; 526/310; 526/312; 526/328.5; 526/347; 526/347.1

(58) Field of Classification Search ............. 525/326.6; 526/277, 279, 307, 307.1, 307.2, 310, 312, 526/328.5, 347, 347.1
See application file for complete search history.

(56) References Cited

U.S. PATENT DOCUMENTS

| 3,453,136 A | 7/1969 | Bylsma et al. |
| 3,497,482 A | 2/1970 | Hwa |
| 3,549,605 A | 12/1970 | Dykstra |
| 3,634,123 A | 1/1972 | Eriksson |
| 3,671,502 A | 6/1972 | Samour et al. |
| 3,861,948 A | 1/1975 | Samour et al. |
| 3,951,893 A | 4/1976 | Gander |
| 4,111,922 A | 9/1978 | Beede et al. |
| 4,205,152 A | 5/1980 | Mizuguchi et al. |
| 4,213,886 A | 7/1980 | Turner |
| 4,722,906 A | 2/1988 | Guire |
| 4,778,865 A | 10/1988 | Leighton |
| 4,863,980 A | 9/1989 | Cowan et al. |
| 4,945,145 A | 7/1990 | Bruylants et al. |
| 4,973,493 A | 11/1990 | Guire |
| 5,002,582 A | 3/1991 | Guire |
| 5,026,490 A | 6/1991 | Peiffer et al. |
| 5,032,455 A | 7/1991 | Dana |
| 5,045,593 A | 9/1991 | Cowan et al. |
| 5,118,524 A | 6/1992 | Thompson et al. |
| 5,162,391 A | 11/1992 | Ikari |
| 5,162,420 A | 11/1992 | Chang et al. |
| 5,177,168 A | 1/1993 | Baron et al. |
| 5,208,295 A | 5/1993 | Chaudhuri et al. |
| 5,223,580 A | 6/1993 | Chaudhuri et al. |
| 5,235,013 A | 8/1993 | Ito et al. |
| 5,264,465 A | 11/1993 | Futamura et al. |
| 5,270,415 A | 12/1993 | Sulc |
| 5,302,669 A | 4/1994 | Furukawa et al. |
| 5,342,621 A | 8/1994 | Eury |
| 5,418,304 A | 5/1995 | Mueller et al. |
| 5,424,375 A | 6/1995 | He |
| 5,453,467 A | 9/1995 | Bamford |
| 5,461,433 A | 10/1995 | Nakabayashi |
| 5,492,989 A | 2/1996 | Chaudhuri et al. |

(Continued)

FOREIGN PATENT DOCUMENTS

CA    1167838    5/1984

(Continued)

OTHER PUBLICATIONS

Fukushima et al., "Interaction Between the Polymer Containing Phosphorylcholine Group and Cells", *Kobunshi Ronbunshu*, vol. 40, No. 12, 1983, pp. 785-793.

Kadoma et al., Synthesis and Hemolysis Test of the Polymer Containing Phosphorylcholine Groups, *Kobunshi Ronbunshu*, vol. 35, No. 7, 1978, pp. 423-427.

(Continued)

*Primary Examiner*—Bernard Lipman
(74) *Attorney, Agent, or Firm*—Sughrue Mion, PLLC

(57) ABSTRACT

A biocompatibilizing process in which a substrate having a surface which bears substrate pendant functional groups is biocompatibilized by coating it with a coating composition containing a polymer formed from a radical polymerizable monomers including a radical polymerisable zwitterionic monomer and a radical polymerizable monomer containing a reactive group to form a polymer having zwitterionic groups and pendant reactive groups and the said pendant reactive groups are reacted to form covalent bonds with said substrate pendant functional group and thereby form a stable coating of polymer on the said surface.

34 Claims, 1 Drawing Sheet

U.S. PATENT DOCUMENTS

| | | | |
|---|---|---|---|
| 5,648,442 | A | 7/1997 | Bowers et al. |
| 5,705,583 | A | 1/1998 | Bowers et al. |
| 5,712,326 | A | 1/1998 | Jones |
| 6,083,257 | A | 7/2000 | Taylor et al. |
| 6,090,901 | A | 7/2000 | Bowers et al. |
| 6,183,506 | B1 | 2/2001 | Penn et al. |
| 6,251,964 | B1 | 6/2001 | Porssa et al. |
| 6,673,883 | B1 | 1/2004 | Rowan |
| 2003/0190405 | A1 | 10/2003 | Bowers et al. |

FOREIGN PATENT DOCUMENTS

| | | |
|---|---|---|
| EP | 0075957 | 4/1983 |
| EP | 0079197 | 5/1983 |
| EP | 0086186 | 8/1983 |
| EP | 0086187 | 8/1983 |
| EP | 192831 | 9/1986 |
| EP | 0208421 | 1/1987 |
| EP | 0293963 | 12/1988 |
| EP | 0350161 | 1/1990 |
| EP | 0412385 | 2/1991 |
| EP | 0537972 | 4/1993 |
| FR | 1549939 | 12/1968 |
| GB | 1529378 | 10/1978 |
| GB | 2113245 | 8/1983 |
| GB | 2161823 | 1/1986 |
| JP | 59-43342 | 3/1984 |
| JP | 60-67489 | 4/1985 |
| JP | 60-21599 | 5/1985 |
| JP | 60-179408 | 9/1985 |
| JP | 60-204711 | 10/1985 |
| JP | 61-205291 | 9/1986 |
| JP | 63-221184 | 9/1988 |
| JP | 3-39309 | 1/1991 |
| JP | 7-051355 | 2/1995 |
| JP | 7-184989 | 7/1995 |
| JP | 7-184990 | 7/1995 |
| JP | 7-284528 | 10/1995 |
| JP | 9-122224 | 5/1997 |
| JP | 9-183819 | 7/1997 |
| WO | WO 90/00887 | 2/1990 |
| WO | WO 92/07885 | 5/1992 |
| WO | WO 093/00391 | 1/1993 |
| WO | WO 93/01221 | 1/1993 |
| WO | WO 93/21970 | 11/1993 |
| WO | WO 97/16133 | 5/1997 |

OTHER PUBLICATIONS

S.M. Park, *Journal of Korean Fiber Society*, vol. 29, No. 10, 1992, pp. 32-37.

Sakurai et al., Macromolecules, vol. 25, No. 26, 1992, pp. 7256-7260.

K. Ishihara et al.., "Journal of Biomedical Materials Research", vol. 24, No. 8, 1990, pp. 1069-1077.

K. Ishihara et al., *Polymer Journal*, vol. 22, No. 5, 1990, pp. 355-360.

Nakabayashi et al., *The 17th Annual Meeting of the Society for Biomaterials*, Scottsdale, AZ (1991).

Campbell et al., "Biocompatible Surfaces Using Methacryloylphosphorylcholine Laurylmethacrylate Copolymer", *ASAIO Journal*, 1994.

Yin et al., "Silicon Secondary Crosslinked IPN Based on poly(Methyl Acrylate-Co-Hydroxyethyl Acrylate) and $SiO_2$", *Polymer*, vol. 38, No. 20, 1997, pp. 5173-5178.

Stratford et al., "Novel Phosphorylcholine Based Hydrogel Polymers: Developments in Medical Device Coatings", *Cardiovascular Division, Biocompatibles Ltd.*

Database WPI, Section Ch., Week 9403, Derwent Publications Ltd., London, GB, AN 94-022958, XP002060534 (Abstract).

Database WPI, Section Ch., Week 9346, Derwent Publications Ltd., London, GB, AN 93-365463, XP002060535 (Abstract).

Database WPI, Section Ch., Week 9312, Derwent Publications Ltd., London, GB, AN 93-096841, XP002060536 (Abstract).

Ishihara et al., "Improvement of Blood Compatibility on Cellulose Dialysis Membrane," *Biomaterials*, vol. 13, No. 3, 1992.

Wielema et al., "Zwitterionic Polymers—I. Synthesis of a Novel Series of Poly(Vinylsulphobetaines). Effect of Structure of Polymer on Solubility in Water," *Eur. Polym. J.*, vol. 23, No. 12, 1987, pp. 947-950.

Ishihara et al.,k "Protein Adsorption from Human Plasma is Reduced on Phospholipid Polymers," *17th Ann. Meet. Soc. Biomaterials*, May, 1991, pp. 297-298.

Kojima et al., "Interaction between Phospholipids and Biocompatible Polymers Containing a Phosphorylcholine Moiety", *Biomaterials*, vol. 12, 1991, pp. 121-124.

Ishihara et al., "Preparation of Phospholipid Polymers and Their Properties as Polymer Hydrogel Membranes", *Polym. J.*, vol. 22, No. 5, 1990, pp. 355-360.

Ishihara et al., "Reduced Thrombogenicity of Polymers Having Phospholipid Polar Groups," *J. Biomed. Materials Res.*, vol. 24, 1990, pp. 1069-1077.

a)

b)

US 7,160,953 B2

POLYMERIC SURFACE COATINGS

This is a continuation of application Ser. No. 10/259,468 filed Sep. 30, 2002, now U.S. Pat. No. 6,743,878 which is a continuation of application Ser. No. 09/002,861 filed Jan. 5, 1998, now abandoned which is a Continuation-in-Part of application Ser. No. 08/475,620 filed Jun. 7, 1995, now U.S. Pat. No. 5,705,583, which was a Continuation-in-Part of application Ser. No. 08/175,348 filed Mar. 7, 1994, now U.S. Pat. No. 5,648,442, which was a Divisional Application of PCT Application No. GB 92/01215 filed Jul. 6, 1992; the disclosures of which are all incorporated herein by reference.

BACKGROUND OF THE INVENTION

The present invention relates to new polymers, processes for producing them and processes for coating surfaces with them. The invention also provides improved processes for producing certain monomers and to certain new monomers used to obtain the polymers. The polymers are useful for coating surfaces of devices and materials which come into contact with protein-containing solutions and biological fluids, and rendering the surfaces bio- and haemocomaptible. Surfaces may thus be rendered suitable for prolonged contact with living tissues and body fluids and with protein-containing solutions.

RELEVANT PRIOR ART

Materials used in the manufacture of separation substrates and devices, blood contacting devices contact and intraocular lenses, and other devices which are used in contact with protein-containing or biological fluids must be selected on the basis of acceptable physical and mechanical properties and compatability with the protein-containing or biological fluid. For any given application of these materials it is usually difficult to optimise all of these considerations simultaneously and a compromise must be reached often resulting in less than optimal performance. For example, major biological problems are often encountered with materials which have otherwise optimal mechanical and physical properties. These problems often manifest themselves as undesirable deposition of biological components and in particular proteinaceous material. This protein adsorption results in blood clot formation in blood-contacting materials, the adsorption of tear components onto contact lenses resulting in deposit formation, formation of deposits on intraocular lenses and in separation media it results in blockage and failure of separation devices. Such effects lead to significant loss in operational performance and often complete rejection and failure of devices.

In the case of medical devices, for example prostheses and components of blood dialysis equipment, it is common practice to employ biocompatible polymers to form at least the surface of the devices to discourage protein adsorption. However, these materials are not perfect and reaction with the living tissues still remains a problem; for example surface-induced thrombosis is still a major difficulty, particularly where large quantities of blood are contacted with a foreign surface such as in artificial lungs and kidneys. Formation of a clot in an artificial organ has a number of adverse or even catastrophic effects including occlusion of the blood pathway in the extracorporeal system, or embolism if the clot breaks off the artificial surface and lodges in a host blood vessel. Dialysis membranes, heart valves, circulator-assist devices, blood substitutes and artificial lungs all share this problem.

It is known that materials for use as biocompatible coatings should ideally:

(a) be capable of reproducible manufacture as pure materials;
(b) be capable of being coated onto surfaces without being degraded or adversely changed;
(c) have the requisite mechanical and permeability properties required for the specific function of the device for which they are intended;
(d) be sterilisable without adverse changes in, for example, permeability and mechanical or surface properties;
(e) not be damaged or degraded by the biological environment;
(f) not be carcinogenic.

In applications involving direct contact with blood further restrictions exist. Materials should not:

(g) induce significant platelet adhesion;
(h) interfere with the normal clotting mechanism; or
(i) cause any significant damage to the cellular elements or soluble components of the blood.

There have been many attempts to prepare biocompatible, and specifically blood compatible (i.e. haemocompatible), surfaces, which do not activate the blood coagulation process and do not promote thrombus formation. Examples of such attempts include the preparation of negatively charged surfaces, such as by use of anionic polymers or suitable oriented electret polymers, preparation of surfaces coated with the natural anticoagulant heparin or synthetic heparin analogues, preparation of surfaces with inherently low surface free energy such as by use of silicone rubber, preparation of albumin-coated surfaces, and preparation of surfaces coated with compounds such as some polymethanes which are thought to adsorb albumin preferentially from blood. All of these however have had limitations.

We have now devised new film-forming polymers which can be used to coat surfaces. It has been found that these copolymers may be used to provide stable coatings on a wide variety of surfaces including, polyethylene, PVC, steel and poly(imide). The invention also provides physiadsorbable polymers which when used to coat surfaces, do not swell, to any significant extent, in aqueous environments; in some situations swelling in aqueous environments can reduce the stability of coatings of physiadsorbable polymers on surfaces.

The polymers which contain zwitterionic groups, mimic the zwitterionic structure of phospholipids such as phosphatidylcholine and sphingomyelin which are the major components of the outer membrane of all living cells. In this way the present invention seeks to provide a biocompatible surface on a coated substrate at which the deposition of proteins and cells at the substrate is minimised when the coated substrate comes into contact with a protein-containing solution or biological fluid.

In addition a variety of ligands may be attached to the polymers of the present invention when coated onto a substrate. Alternatively ligands may be attached to the polymers prior to coating on a substrate, e.g. when the polymer is in solution. The polymers of the present invention may therefore provide a means of attachment of such ligands. The term ligand includes, but is not limited to, specific binding agents such as immunoglobulins and associated fragments thereof such as those useful for affinity separation and diagnostic applications, photosensitive and chemisensitive moieties such as those useful for detector and sensor applications and therapeutic agents useful for clinical applications. Other ligands include peptide fragments which may be chemically linked to a polymer of the invention, such as fragments which induce cell attachment and may therefore be used to allow the polymers of the present invention to provide cell seeding.

SUMMARY OF THE INVENTION

The present invention provides a polymer of one or more radical polymerisable, preferably ethylenically unsaturated, monomers, which polymer has pendant zwitterionic groups bearing a centre of permanent positive charge and other pendant groups capable of stably binding the polymer to a surface. Such coatings bind to surfaces with good adhesion and are not removable in the environment in which the coated surfaces are used, e.g. in use as a coating on a blood-contacting surface.

Zwitterionic groups mimic the structure of the head groups of phospholipids in cells. Without wishing to be limited by this theory, it is thought that the presence of such groups at a surface renders the surface more biocompatible.

The extent to which a polymer renders a surface biocompatible may be assessed as a combination of factors such as reduction in the extent to which the surface causes blood platelet activation, protein adsorption, (for instance as judged by absorption of fibrinogen from human plasma) and reaction with C-reactive protein which is caused by the presence on the surface of isolated zwitterionic, e.g.) phosphate ammonium ester groups. Preferably the polymers of the invention when coated onto a substrate, provide a reduction in platelet activation of at least 70%, more preferably at least 90%, as assessed by the assay described hereinafter compared to an untreated substrate. It is also preferred that the polymers of the invention, when coated onto a substrate, provide a reduction in fibrinogen absorption of at least 60% as assessed by the assay described hereinafter and a protein index of less than $1.5 \times 10^4$ compared to an untreated substrate. The protein index is defined as the ratio of the absorbance due to C-reactive protein measured in the assay described hereinafter to the reduction in fibrinogen adsorption.

The nature of the groups capable of binding the polymer to a surface will be selected depending upon the nature of the surface which it is intended to coat with the polymer. Where the surface is hydrophobic, groups capable of being physisorbed at the surface may be used to bind the polymer to the surface. Where the surface is hydrophilic and bears functional groups then groups which are capable of reacting with surface functional groups to form covalent bonds may be used to bind the polymer to the surface. Where the surface is charged then groups bearing ionic charge may be used to bind the polymer to the surface by ionic interactions.

Polymers of the invention may therefore bind to a surface by physisorption, covalent or ionic bonding depending upon the precise nature of the surface. In certain cases it may be possible to use two of these binding mechanisms in combination.

In the present invention the polymer must include reactive groups capable of forming covalent bonds with a substrate surface of with coreactive groups on the polymer to crosslink it at the surface after coating. For polymers which cross-link initial surface binding may be provided by hydrophobic or ionic bonding.

It will be understood that throughout, where a group is referred to as capable of binding a polymer to a surface this is intended to mean stably binding.

Where a hydrophobic surface is to be coated, alkyl groups of 6 or more carbon atoms, or fluoroalkyl groups, optionally having one or more etheric oxygen atoms interrupting the carbon chain, and optionally containing one or more carbon-carbon double or triple bonds, or siloxane groups, preferably containing from 1 to 50, more preferably 5 to 30, silicon atoms, may be used as the pendant groups capable of binding the polymer to a surface. Such groups are capable of forming strong secondary valence interactions with a surface, and being physisorbed at a hydrophobic surface, i.e. adsorbed without formation of a covalent interaction.

Thus according to the invention there is provided a polymer obtainable by:

(i) copolymerising a radical polymerisable, preferably ethylenically unsaturated, zwitterionic comonomer and a radical polymerisable, preferably ethylenically unsaturated, comonomer bearing a reactive group; or (ii) polymerising a radical polymerisable, preferably ethylenically unsaturated, monomer containing a zwitterionic group and a reactive group capable of covalently binding the polymer to a surface.

Such a polymer may be a copolymer comprising residues of a radical polymerisable, preferably ethylenically unsaturated, comonomer containing a group bearing a centre of permanent positive charge and a radical polymerisable, preferably ethylenically unsaturated, the comonomer bearing a reactive group is capable of covalently binding to a surface, and/or of crosslinking the polymer.

In the specification the definitions of groups as reactive and as functional are intended to be of the same scope unless the context indicates otherwise.

BRIEF DESCRIPTION OF THE DRAWINGS

FIG. 1.(*b*) shows a scanning electron micrograph (900×) of a poly(acrylic acid) subbed poly(imide) sheet treated with poly(2(methylacryloyloxyethyl)-2(trimethylammonium) ethyl phosphate-co-2-aminomethacrylate) (9:1), in accordance with Example 2.

DETAILED DESCRIPTION OF THE INVENTION

Figure 1:
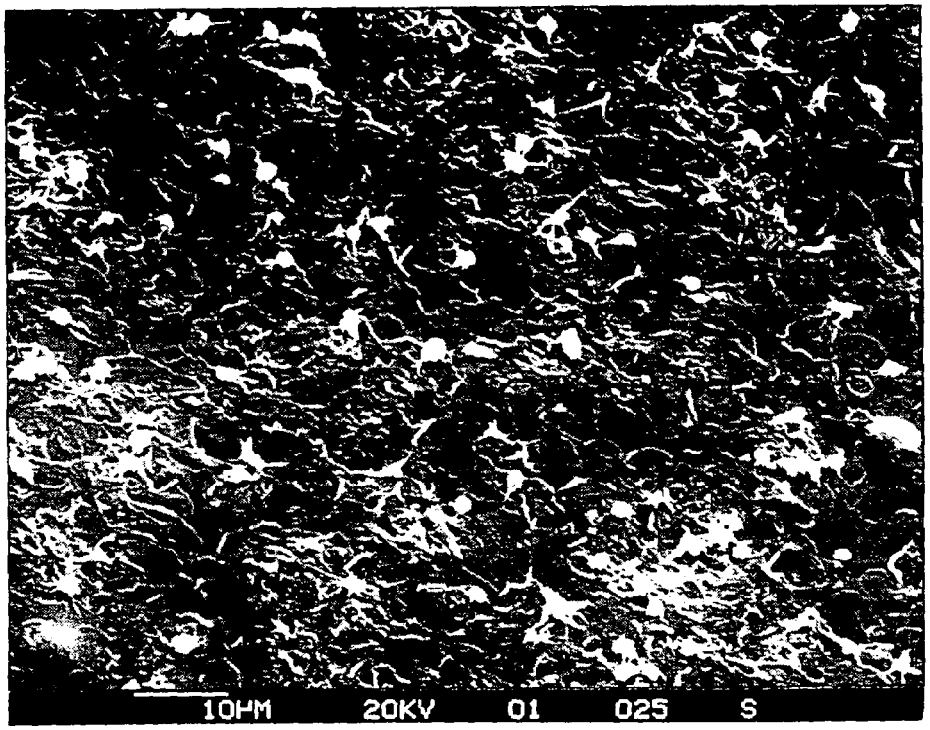
FIG. 1.(*a*) shows a scanning electron micrograph (1200×) of an unsubbed, untreated poly(imide) sheet.
Figure 1:
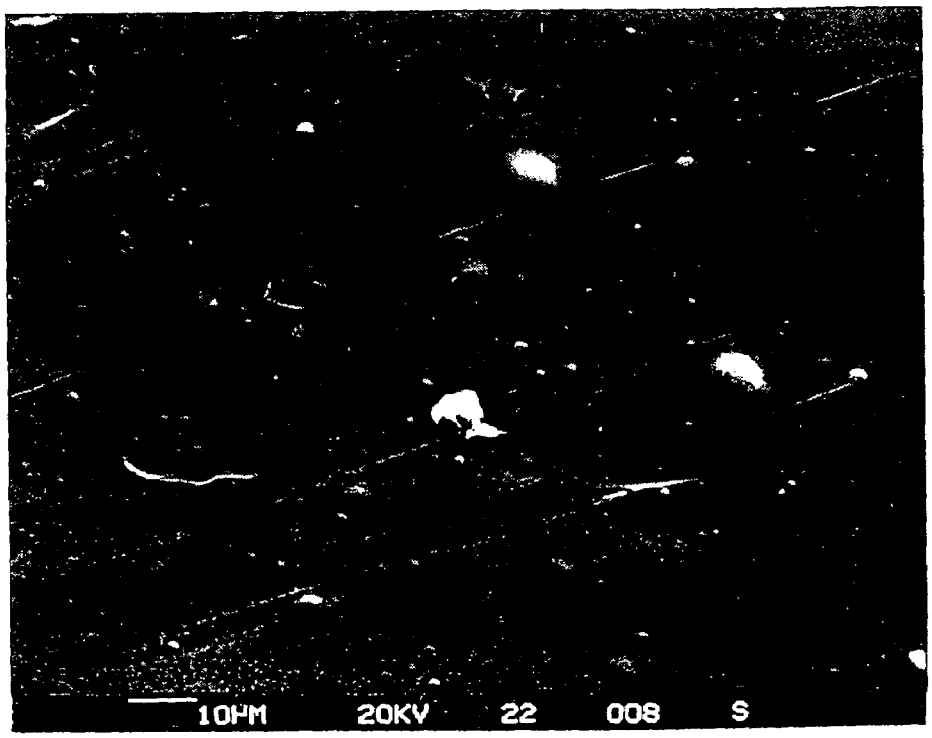

The invention is directed to a process of coating in which a coating composition contains a substantially non-crosslinked polymer formed by radical polymerisation of radical polymerisable monomers including i) a zwitterionic monomer having the formula:

$$Y-B-X \quad (I)$$

wherein B is a straight or branched alkylene, oxaalkylene or oligo-oxaalkylene chain optionally containing one or more fluorine atoms up to and including perfluorinated chains, or if X contains a carbon-carbon chain between B and the centre of permanent position charge or if Y contains a terminal carbon atom bonded to B, a valence bond;

X is a zwitterionic group selected from groups IVB, IVC, IVD, IVE and IVF in which group IVB has the formula

wherein the groups $R^6$ are the same or different and each is hydrogen or $C_{1-4}$ alkyl and d is from 2 to 4;

group IVC has the formula

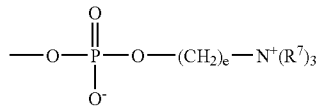

where the groups $R^7$ are the same or different and each is hydrogen or $C_{1-4}$ alkyl, and e is from 1 to 4;

group IVD has the formula

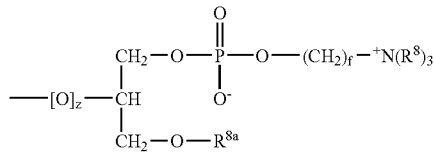

wherein the groups $R^8$ are the same or different and each is hydrogen or $C_{1-4}$ alkyl, $R^{8a}$ is hydrogen or a group —C(O)$B^1R^{8b}$ wherein $R^{8b}$ is hydrogen or methyl, $B^1$ is a valence bond or straight or branched alkylene, oxaalkylene or oligo-oxaalkylene group, and f is from 1 to 4; and if B is other than a valence bond z is 1 and if B is a valence bond z is 0, if X is directly bonded to an oxygen or nitrogen atom and otherwise z is 1;

group IVE has the formula

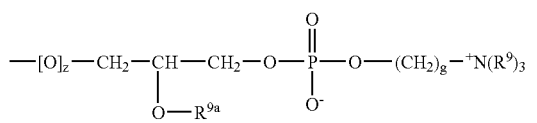

wherein the groups $R^9$ are the same or different and each is hydrogen or $C_{1-4}$ alkyl, $R^{9a}$ is hydrogen or a group —C(O)$B^2R^{9b}$, wherein $R^{9b}$ is hydrogen or methyl, $B^2$ is a valence bond or a straight or branched alkylene, oxaalkylene or oligo-oxaalkylene group, and g is from 1 to 4; and if B is other than a valence bond z is 1 and if B is a valence bond z is 0 if X is directly bonded to an oxygen or nitrogen atom and otherwise z is 1; and group IVF has the formula

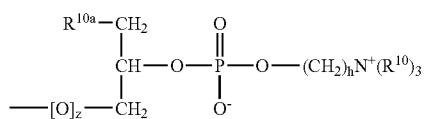

wherein the groups $R^{10}$ are the same or different and each is hydrogen or $C_{1-4}$ alkyl, $R^{10a}$ is hydrogen or a group —C(O)$B^3R^{10b}$ wherein $R^{10b}$ is hydrogen or methyl, $B^3$ is a valence bond or a straight or branched alkylene, oxaalkylene or oligo-oxaalkylene group, and h is from 1 to 4; and if B is other than a valence bond z is 1 and if B is a valence bond z is 0 if X is directly bonded to the oxygen or nitrogen and otherwise z is 1 and Y is an ethylenically unsaturated polymerisable group selected from

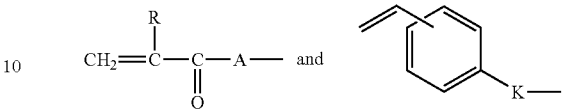

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are as defined above; and K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—, (in which the groups $R^2$ are the same or different) —$(CH_2)_pO$—, —$(CH_2)_pSO_3$—, or, optionally in combination with B, a valence bond and p is from 1 to 12 and $R^2$ is hydrogen or a $C_1$–$C_4$ alkyl group and ii) a monomer having a reactive group of the formula general formula (XII)

$$Y^2-B^7-Q^3 \qquad (XII)$$

where $Y^2$ is an ethylenically unsaturated polymerisable group selected from

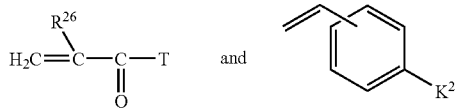

where $R^{26}$ is hydrogen or $C_1$–$C_4$ alkyl;

T is —O— or $NR^{27}$—, wherein $R^{27}$ is hydrogen or a $C_1$–$C_4$ alkyl group or $R^{27}$ is a group —$B^7Q^3$;

$B^7$ is a valence bond a straight or branched alkylene oxaalkylene or oligo-oxaalkylene group;

$K^2$ is a group —$(CH_2)_qOC(O)$—, —$(CH)_qC(O)O$—, —$(CH_2)_qOC(O)O$—, —$(CH_2)_qNR^{20}$—, —$(CH_2)_qNR^{20}C(O)$—, —$(CH_2)_qC(O)NR^{20}$—, —$(CH_2)_qNR^{20}C(O)O$—, —$(CH_2)_qOC(O)NR^{20}$—, —$(CH_2)_qNR^{20}C(O)NR^{20}$— (in which the groups $R^{20}$ are the same or different), —$(CH_2)_qO$—, or —$(CH_2)_qSO_4$—, or a valence bond and q is from 1 to 12 and $R^{20}$ is hydrogen or a $C_1$–$C_4$ alkyl group; and $Q^3$ is a reactive group selected from the group consisting of aldehyde groups; silane and siloxane groups containing one or more substituents selected from halogen atoms and $C_{1-4}$-alkoxy groups; hydroxyl; amino; carboxyl; epoxy; —CHOHCH$_2$Hal (in which Hal is selected from chlorine, bromine and iodine atoms); succinimido; tosylate; triflate; imidazole carbonyl amino; optionally substituted triazine groups; cinnamyl; ethylenically and acetylenically unsaturated groups; acetoacetoxy; methylol; and chloroalkylsulphone groups; acetoxy; mesylate; carbonyl di(cycloalkyl carbodiimidoyl; and oximino;

is coated onto a substrate surface having pendant reactive group and, after coating, the pendant reactive groups or polymer and surface are reacted whereby covalent bonds are formed between the polymer and the substrate.

Preferred groups $Q^3$ are aldehyde, reactive silane and siloxane, amino, epoxy, $CHOHCH_2Hal$ (in which Hal is halogen), succimimido, tosylate, triflate, imidazolecarbonyl amino and optionally substituted triazine groups.

In one embodiment the polymer is obtainable by (i) copolymerising the zwitterionic monomer, the monomer having a reactive group and a radical polymerisable, preferably an ethylenically unsaturated, comonomer containing a radical polymerisable moiety and an alkyl group of 6 or more carbon atoms, which alkyl group optionally contains one or more etheric oxygen atoms and optionally one or more carbon-carbon double or triple bonds, or a fluoroalkyl group which optionally contains one or more etheric oxygen atoms and optionally one or more carbon-carbon double or triple bonds, or a siloxane group; or (ii) polymerising a radical polymerisable, preferably ethylenically unsaturated, monomer containing a zwitterionic group and an alkyl group of 6 or more carbon atoms, which alkyl group optionally contains one or more etheric oxygen atoms, or a fluoroalkyl group which optionally contains one or more etheric oxygen atoms, or a siloxane group with the comonomer having a reactive group.

In this embodiment, preferably the polymer is a copolymer comprising residues of a comonomer containing a physisorbable group and as well as the zwitterionic monomer and monomer having a reactive group.

It is also preferred that the physisorbable group is an alkyl or fluoroalkyl group optionally containing one or more carbon-carbon double or triple bonds. Such a group may contain one or more etheric oxygen atoms, but in an especially preferred embodiment does not contain any etheric oxygen atoms.

In one embodiment, where the physisorbable group is an alkyl or fluoroalkyl group, optionally containing one or more etheric oxygen atoms; this group does not contain any carbon-carbon double or triple bonds.

Where a hydrophillic surface having functional groups is to be coated, groups capable of covalently binding the polymer to the surface may be incorporated into the polymer as pendant groups.

Where a surface bearing an ionic charge is to be coated, ionic groups, capable of binding the polymer to the surface by ionic interactions, may be incorporated into the polymer of the invention as pendant groups.

According to a preferred embodiment, the polymer is obtainable by i) copolymerising the zwitterionic monomer, the monomer having a reactive group and a radical polymerisable, preferably ethylenically unsaturated, comonomer bearing an ionic group capable of binding to a surface by ionic interaction; or (ii) polymerising a radical polymerisable, preferably ethylenically unsaturated, monomer containing a zwitterionic group bearing a centre of permanent positive charge, which is preferably zwitterionic, and an ionic group capable of binding to a surface by ionic interaction with the comonomer having a reactive group.

Optionally, in any of the above embodiments, the polymers also comprise residues of one or more diluent monomers.

The invention also provides a process for producing such a polymer which comprises polymerising such monomers and a process for coating a surface with such a polymer, for instance a process comprising the steps of (a) polymerising such monomers to form the polymer and (b) coating the surface with the polymer so formed. Optionally, the process further comprises attaching a ligand to the polymer either in solution before coating the surface, or, more preferably when coated on the surface.

In a specific embodiment the invention further provides such polymers containing residues of a crosslinkable monomer, which are uncrosslinked, when either coated on a surface or not coated on a surface and such polymers which are crosslinked when coated on a surface. The invention further provides a process of crosslinking such polymers when coated on a surface.

As yet a further feature, the present invention provides certain new monomers useful in producing the polymers of the invention.

Monomers and comonomers which may be used in the polymers of the invention will now be described in more detail.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Zwitterionic Monomers

The zwitterionic monomer (or comonomer) bears a centre of permanent positive charge and also a centre of negative charge. Typically the centre of permanent positive charge is provided by a quaternary nitrogen atom.

Preferred comonomers which bear a centre of positive charge are of general formula (I)

wherein B is a straight or branched alkylene, oxaalkylene or oligo-oxaalkylene chain optionally containing one or more fluorine atoms up to and including perfluorinated chains or, if X contains a carbon-carbon chain between B and the centre of permanent positive charge or if Y contains a terminal carbon atom bonded to B, a valence bond;

X is a zwitterionic group and

Y is an ethylenically unsaturated polymerisable group selected from

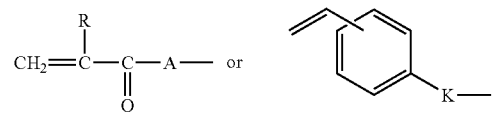

wherein:

R is hydrogen or a $C_1$–$C_4$ alkyl group;

A is —O— or —$NR^1$— where $R^1$ is hydrogen or a $C_1$–$C_4$ alkyl group or $R^1$ is —B—X where B and X are as defined above; and K is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)O$—, —$(CH_2)_pOC(O)NR^2$—, —$(CH_2)_pNR^2C(O)NR^2$—, (in which the groups $R^2$ are the same or different) —$(CH_2)_p$ O—, —(CH$_2$)$_p$SO$_3$—, or, optionally in combination with B, a valence bond and p is from 1 to 12 and R$^2$ is hydrogen or a C$_1$–C$_4$ alkyl group.

The proviso on whether B may be a valence bond ensures that the zwitterionic group X is not directly bonded to a heteroatom, such as an oxygen or nitrogen atom in Y.

Preferred zwitterionic monomers containing a group bearing a centre of permanent positive charge are therefore of general formula (II) or (III).

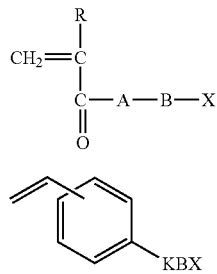

(II)

(III)

where R, A, B, K and X are as defined with reference to formula (I).

Preferably in the compounds of formula (II) R is hydrogen, methyl, or ethyl, more preferably methyl, so that (II) is an acrylic acid, methacrylic acid or ethacrylic acid derivative.

In the compounds of formula (III) K may be a valence bond and B a group, K may be a group and B a valence bond, both K and B may be groups, or K and B may together be a valence bond.

Preferably B is a group where K is a valence bond.

Where K is a group then preferably p is from 1 to 6, more preferably 1, 2 or 3 and most preferably p is 1. When K is a group —(CH$_2$)$_p$NR$^2$—, —(CH$_2$)$_p$NR$^2$C(O)—, —(CH$_2$)$_p$C(O)NR$^2$, —(CH$_2$)$_p$NR$^2$C(O)O—, —(CH$_2$)$_p$OC(O)NR$^2$— or —(CH$_2$)$_p$NR$^2$C(O)NR$^2$— then R$^2$ is preferably hydrogen, methyl or ethyl, more preferably hydrogen.

In the compounds of formula (III) preferably the vinyl group is para to the group —K—B—X.

Preferably B is:

an alkylene group of formula —(CR$^3$$_2$)$_a$—, wherein the groups —(CR$^3$$_2$)$_a$— are the same or different, and in each group —(CR$^3$$_2$)$_a$— the groups R$^3$ are the same or different and each group R$^3$ is hydrogen, fluorine or C$_{1-4}$ alkyl or fluroalkyl, preferably hydrogen, and a is from 1 to 12, preferably 1 to 6;

an oxaalkylene group such as alkoxyalkyl having 1 to 6 carbon atoms in each alkyl moiety, more preferably —CH$_2$O(CH$_2$)$_4$—; or an oligo-oxaalkylene group of formula —[(CR$^4$$_2$)$_b$O]$_c$(CR$^4$$_2$)$_b$— where the groups —(CR$^4$$_2$)— are the same or different and in each group —(CR$^4$$_2$)— the groups R$^4$ are the same or different and each group R$^4$ is hydrogen, fluorine or C$_{1-4}$ alkyl or fluoroalkyl, preferably hydrogen, and b is from 1 to 6, preferably 2 or 3 and c is from 2 to 11, preferably 2 to 5; or if X contains a carbon-carbon chain between B and the zwitterionic group if Y contains a terminal carbon atom, a valence bond.

Preferred groups B include alkylene, oxaalkylene and oligo-oxaalkylene groups of up to 12 carbon atoms optionally containing one or more fluorine atoms. Where the polymer is not intended for coating a hydrophobic surface, and therefore is not intended to be bound by physiosorption to a surface, then preferably B is an alkylene, oxaalkylene or oligo-oxaalkylene group which does not contain any fluorine atoms.

In compounds of formula (III) it is preferred that K and B contain up to 12 carbon atoms in total.

Preferred groups X containing a zwitterionic group, are the groups of formula (IVA), (IVB), (IVC), (IVD), (IVE) and (IVF) as defined below: monomers containing such groups may be used in combination with further monomers containing groups capable of binding to a surface, to provide a copolymer of the invention. Of these groups of formula (IVC) are particularly preferred.

In addition, groups of formula (VA), (VB) and (VC) are preferred as zwitterionic monomers further having an alkyl, fluoroalkyl or siloxane group capable of binding to a surface by physisorption.

The groups of formula (IVB) are:

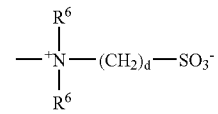

(IVB)

where the groups R$^6$ are the same or different and each is hydrogen or C$_{1-4}$ alkyl and d is from 2 to 4.

Preferably the groups R$^6$ are the same. It is also preferable that at least one of the groups R$^6$ is methyl, and more preferable that the groups R$^6$ are both methyl.

Preferably d is 2 or 3, more preferably 3.

When X is a group of formula (IVB) preferably B is a group of formula —(CR$^3$$_2$)— or —(CR$^3$$_2$)$_2$ eg. —(CH$_2$)— or —(CH$_2$CH$_2$)—.

The groups of formula (IVC) are:

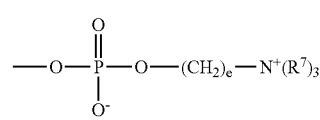

(IVC)

where the groups R$^7$ are the same or different and each is hydrogen or C$_{1-4}$ alkyl, and e is from 1 to 4.

Preferably the groups R$^7$ are the same. It is also preferable that at least one of the groups R$^7$ is methyl, and more preferable that the groups R$^7$ are all methyl.

Preferably e is 2 or 3, more preferably 2. When X is a group of formula (IVC) preferably B is a group of formula —(CR$^3$$_2$)— or —(CR$^3$$_2$)$_2$—, eg. —(CH$_2$)— or —(CH$_2$CH$_2$)—.

The groups of formula (IVD) are:

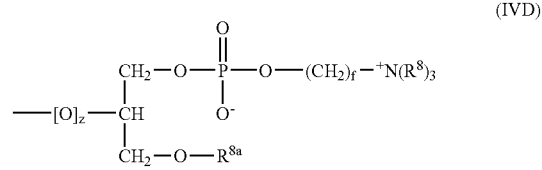

(IVD)

wherein the groups $R^8$ are the same or different and each is hydrogen or $C_{1-4}$ alkyl, $R^8$— is hydrogen or, more preferably, a group —$C(O)B^1R^{8b}$ where $R^{8b}$ is hydrogen or methyl, preferably methyl, $B^1$ is a valence bond or straight or branched alkylene, oxaalkylene or oligo-oxaalkalyene group, and f is from 1 to 4; and if B is other than a valence bond Z is 1 and if B is a valence bond Z is O, if X is directly bonded to an oxygen or nitrogen atom and otherwise Z is 1.

Preferably the groups $R^8$ are the same. It is also preferable that at least one of the groups $R^8$ is methyl, and more preferable that the groups R8 are all methyl.

Preferably f is 1 or 2, more preferably 2.

Preferably $B^1$ is:

a valence bond;

an alkylene group of formula —$(CR^{3a}_2)_{aa}$—, wherein the groups —$(CR^{3a}_2)$— are the same or different, and in each group $(CR^{3a}_2)$— the groups $R^{3a}$— are the same or different and each group $R^{3a}$— is hydrogen or $C_{1-4}$ alkyl, preferably hydrogen, and aa is from 1 to 12, preferably 1 to 6;

an oxaalkylene group such as alkoxyalkyl having 1 to 6 carbon atoms in each alkyl moiety, more preferably —$CH_2O(CH_2)_4$—; or an oligo-oxaalkylene group of formula —$[(CR^{4a}_2)_{ba}O]_{ca}$— where the groups —$(CR^{4a}_2)$— are the same or different and in each group —$(CR^{4a}_2)$— the groups $R^{4a}$ are the same or different and each group $R^{4a}$ is hydrogen or $C_{1-4}$ alkyl, preferably hydrogen, and ba is from 1 to 6, preferably 2 or 3, and ca is from 1 to 12, preferably 1 to 6.

Preferred groups $B^1$ include a valence bond and alkylene, oxaalkylene and oligo-oxaalkylene groups of up to 12 carbon atoms.

Preferably B and $B^1$ are the same.

When X is a group of formula (IVD) preferably B is a group of formula —$[(CR^4_2CR^4_2)_cO_b]CR^4_2CR^4_2$—, eg. —$(CH_2CH_2O)_c(CH_2CH_2)$—.

The groups of formula (IVE) are:

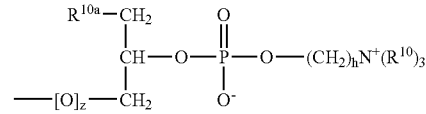

(IVE)

wherein the groups $R^9$ are the same or different and each is hydrogen or $C_1$–$C_4$ alkyl, $R^{9a}$ is a hydrogen or, more preferably, a group —$C(O)B^2R^{9b}$, $R^{9b}$ is hydrogen or methyl, preferably methyl, $B^2$ is a valence bond or a straight or branched alkylene, oxaalkylene or oligo-oxaalkylene group, and g is from 1 to 4; and if B is other than a valence bond Z is 1 and if B is a valence bond Z is O if X is directly bonded to an oxygen or nitrogen atom and otherwise Z is 1.

Preferably the groups $R^9$ are the same. It is also preferable that at least one of the groups $R^9$ is methyl, and more preferable that the groups $R^9$ are all methyl.

Preferably g is 1 or 2, more preferably 2.

Preferably $B^2$ is:

a valence bond;

an alkylene group of formula —$(CR^{3b}_2)_{ab}$—, wherein the groups —$(CR^{3b}_2)$— are the same or different, and in each group —$(CR^{3b}_2)$— the groups $R^{3b}$ are the same of different and each group $R^{3b}$ is hydrogen or $C_{1-4}$ alkyl, preferably hydrogen, and ab is from 1 to 12, preferably 1 to 6;

an oxaalkylene group such as alkoxyalkyl having 1 to 6 carbon atoms in each alkyl moiety, more preferably —$CH_2O(CH_2)_4$—; or an oligo-oxaalkylene group of formula —$[(CR^{4b}_2)_{bb}O]_{cb}$— where the groups —$(CR^{4b}_2)$— are the same or different and in each group —$(CR^{4b}_2)$— the groups $R^{4b}$ are the same or different and each group $R^{4b}$ is hydrogen or $C_{1-4}$ alkyl, preferably hydrogen, and bb is from 1 to 6, preferably 2 or 3, and cb is from 1 to 12, preferably 1 to 6.

Preferred groups $B^2$ include a valence bond and alkylene, oxalkylene and oligo-oxalkylene groups of up to 12 carbon atoms.

Preferably B and $B^2$ are the same.

When X is a group of formula (IVE) preferably B is a group of formula —$[(CR^4_2CR^4_2)_bO]_cCR^4_2CR^4_2$—, eg. —$(CH_2CH_2O)_cCH_2CH_2$—.

The groups of formula (IVF) are:

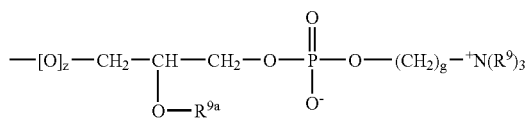

(IVF)

wherein the groups $R^{10}$ are the same or different and each is hydrogen or $C_{1-4}$ alkyl, $R^{10a}$ is hydrogen or, more preferably, a group —$C(O)B^3R^{10b}$ where $R^{10b}$ is hydrogen or methyl, preferably methyl, $B^3$ is a valence bond or a straight or branched alkylene, oxaalkylene or oligo-oxaalkylene group, and h is from 1 to 4; and if B is other than a valence bond Z is 1 and if B is a valence bond Z is O if X is directly bonded to the oxygen or nitrogen and otherwise Z is 1.

Preferably the groups $R^{10}$ are the same. It is also preferable that at least one of the groups $R^{10}$ is methyl, and more preferable that the groups $R^{10}$ are all methyl.

Preferably h is 1 or 2, more preferably 2.

Preferably $B^2$ is:

a valence bond;

an alkylene group of formula —$(CR^{3c}_2)_{ac}$—, wherein the groups —$(CR^{3c}_2)$— are the same or different and in each group $(CR^{3c}_2)$— the groups $R^{3c}$ are the same or different and each group $R^{3c}$ is hydrogen or $C_{1-4}$ alkyl, preferably hydrogen, and ac is from 1 to 12, preferably 1 to 6;

an oxaalkylene group such as alkoxyalkyl having 1 to 6 carbon atoms in each alkyl moiety, more preferably —$CH_2O(CH_2)_4$—; or an oligo-oxaalkylene group of formula —$[(CR^{4c}_2)_{bc}O]_{cc}$— where the groups —$(CR^{4c}_2)$— are the same or different and in each group —$(CR^{4c}_2)$— the groups $R^{4c}$ are the same or different and each group $R^{4c}$ is hydrogen or $C_{1-4}$ alkyl, preferably hydrogen, and bc is from 1 to 6, preferably 2 or 3, and cc is from 1 to 12, preferably 1 to 6.

Preferred groups $B^3$ include a valence bond and alkylene, oxaalkylene and oligo-oxaalkylene groups of up to 12 carbon atoms.

Preferably B and $B^3$ are the same.

When X is a group of formula (IVF) preferably B is a group of formula —$[(CR^4_2CR^4_2)_bO]_cCR^4_2CR^4_2$—, eg. —$(CH_2CH_2O)_cCH_2CH_2$—.

Further zwitterionic groups are of formula (VA), (VB) and (VC). These groups also contain an alkyl or fluoroalkyl group capable of binding to a surface by physisorption. Monomers containing such a group are therefore particularly suitable for use in the polymers of the invention, optionally without separate comonomers containing a group capable of binding to a hydrophobic surface by physisorption.

The groups of formula (VA) are:

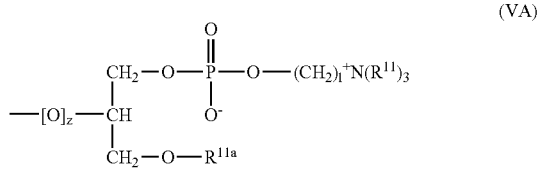

wherein the groups $R^{11}$ are the same or different and each is hydrogen or $C_{1-4}$ alkyl, $R^{11a}$ is either (a) a group $-[C(O)]_{vw}(CR^{11b}{}_2)_{ww}(SiR^{11c}{}_2)(OSiR^{11c}{}_2)_{vv}R^{11c}$ in which each group $R^{11b}$ is the same or different and is hydrogen or alkyl of 1 to 4 carbon atoms, each group $R^{11c}$ is the same or different and is alkyl of 1 to 4 carbon atoms or aralkyl, for example benzyl or phenethyl, vw is 0 or 1, ww is from 0 to 6 with the proviso that vw and ww are not both 0, and vv is from 0 to 49;

(b) a group of formula $-C(O)B^4-R^{11d}$, in which $R^{11d}$ is hydrogen or methyl, $B^4$ is a valence bond or straight or branched alkylene, oxaalkylene or oligo-oxaalkalyene group optionally containing one or more fluorine atoms, and containing from 6 to 24, preferably 6 to 18 carbon atoms;

i is from 1 to 4; and if B is other than a valence bond Z is 1 and if B is a valence bond Z is 0 if X is directly bonded to an oxygen or nitrogen atom and otherwise Z is 1.

Preferably the groups $R^{11}$ are the same. It is also preferable that at least one of the groups $R^{11}$ is methyl, and more preferable that the groups $R^{11}$ are all methyl.

Preferably i is 1 or 2, more preferably 2.

Where $R^{11a}$ is a siloxane group as defined in (a) above, each group $(CR^{11b}{}_2)$ may be the same or different, preferably the same, and preferably each group $R^{11b}$ is hydrogen. Preferably ww is from 2 to 4, and is most preferably 3 when vw is 0 or 2 when vw is 1. Each group $(SiR^{11c}{}_2)$ may be the same or different, preferably the same, and preferably each group $R^{11d}$ is methyl.

Preferably vv is from 4 to 29.

Preferably the group $R^{11a}$ is a group $-C(O)B^4R^{11d}$ as defined above. In such a case, preferably $B^4$ is:

a valence bond;

an alkylene group of formula $-(CR^{3d}{}_2)_{ad}-$ wherein the groups $-(CR^{3d}{}_2)-$ are the same or different, and in each group $-(CR^{3d}{}_2)-$ the groups $R^{3d}$ are the same or different and each group $R^{2d}$ is hydrogen, fluorine or $C_{1-4}$ alkyl or fluoroalkyl, preferably hydrogen or fluorine, and ad is from 1 to 24, preferably to 18;

an oxaalkylene group such as alkoxyalkyl having 1 to 6 carbon atoms and optionally one or more fluorine atoms in each alkyl moiety, or an oligo-oxalkylene group of formula $-[(CR^{4d}{}_2)_{bd}O]_{cd}-$ where the groups $-(CR^{4d}{}_2)-$ are the same or different and in each group $-(CR^{4d}{}_2)-$ the groups $R^{4d}$ are the same or different and each group $R^{4d}$ is hydrogen, fluorine or $C_{1-4}$ alkyl or fluoroalkyl, preferably hydrogen or fluorine, and bd is from 2 to 6, preferably 3 or 4, and cd is from 1 to 12, preferably 1 to 6.

When $B^4$ is a group $-[(CR^{4d}{}_2)_{bd}O]_{cd}-$ wherein all the groups $R^{4d}$ are hydrogen and in all the groups $-[(CR^{4d}{}_2)_{bd}O]-$ bd is 2, the residues of the monomer of formula (VA) are not able to form strong secondary valence interactions with hydrophobic surfaces. Whilst residues of such monomers may be included in the polymers of the invention, it is usually also necessary to include residues of monomers which are capable of forming strong secondary valence interactions if such interactions are to bind a polymer to a surface.

Monomers which have groups containing oligo(higher alkylene) oxide moieties can be used to provide strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that there are more propylene oxide units than ethylene oxide units.

When $B^4$ is a group $-[(CR^{4d}{}_2)_{bd}O]_{cd}-$ then preferably bd is 2 in only 50, preferably 70, more preferably 90 mole % or less of the residues $-[(CR^{4d}{}_2)_{bd}O]-$.

When the group $-B^4-R^{11a}$ is a group capable of forming strong secondary valence interactions with a surface, then monomers containing a group (VA) may be particularly suitable for use as zwitterionic monomer and an alkyl or fluoroalkyl group optionally containing one or more etheric oxygen atoms. Preferably, in such a case $-B^4-R^{11a}$ is an alkyl group optionally containing one or more etheric oxygen atoms and preferably 6 or more carbon atoms or a fluoroalkyl group optionally containing one or more etheric oxygen atoms and preferably 6 or more carbon atoms.

In one embodiment B and $B^4$ may be the same.

The groups of formula (VB) are:

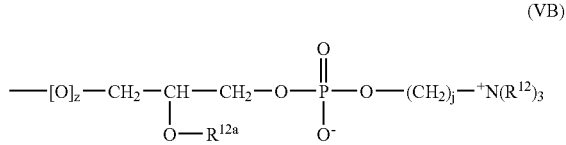

wherein the groups $R^{12}$ are the same or different and each is hydrogen or $C_1-C_4$ alkyl, $R^{12a}$ is either (a) a group $-[C(O)]_{tu}(CR^{12b}{}_2)_{uu}(SiR^{12c}{}_2)(OSiR^{12c}{}_2)_{tt}R^{12c}$ in which each group $R^{12b}$ is the same or different and is hydrogen or alkyl of 1 to 4 carbon atoms, each group $R^{12c}$ is the same or different and is alkyl of 1 to 4 carbon atoms or aralkyl, for example benzyl or phenethyl, tu is 0 or 1, uu is from 0 to 6, with the proviso that tu and uu are not both 0, and tt is from 0 to 49; or (b) a group of formula $-C(O)B^5-R^{12d}$, in which $R^{12d}$ is hydrogen or methyl, $B^5$ is a valence bond or a straight or branched alkylene, oxaalkylene or oligo-oxaalkylene group optionally containing one or more fluorine atoms and from 6 to 24 carbon atoms, more preferably 6 to 18 carbons atoms, j is from 1 to 4; and if B is other than a valence bond, Z is 1 and if B is a valence bond Z is 0 if X is directly bonded to an oxygen or nitrogen atom and otherwise Z is 1. Preferably the groups $R^{12}$ are the same. It is also preferable that at least one of the groups $R^{12}$ is methyl, and more preferable that the groups $R^{12}$ are all methyl.

Preferably j is 1 or 2, more preferably 2.

Where $R^{12a}$ is a siloxane group as defined in (a) above, each group $(CR^{12b}{}_2)$ may be the same or different, preferably the same, and preferably each group $R^{12b}$ is hydrogen. Preferably uu is from 2 to 4, and is most preferably 3 when tu is 0 or 2 when tu is 1. Each group $(SiR^{12c}_2)$ may be the same or different, preferably the same, and preferably each group $R^{12c}$ is methyl.

Preferably tt is from 4 to 29.

Preferably the group $R^{12a}$ is a group —C(O)B$^4$R$^{12d}$ as defined above. In such a case, preferably B$^5$ is:

a valence bond;

an alkylene group of formula —(CR$^{8e}_2$)$_{ae}$—, wherein the groups —(CR$^{3e}_2$)— are the same or different, and in each group —(CR$^{3e}_2$)— the groups R$^{3e}$ are the same of different and each group R$^{3e}$ is hydrogen, fluorine or C$_{1-4}$ alkyl, or fluoroalkyl, preferably hydrogen or fluorine, and ae is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula —[(CR$^{4e}_2$)$_{be}$O]$_{ce}$— where the groups —(CR$^{4e}_2$)— are the same or different and in each group —(CR$^{4e}_2$)— the groups R$^{4e}$ are the same or different and each group R$^{4e}$ is hydrogen, fluorine or C$_{1-4}$ alkyl or fluoroalkyl, preferably hydrogen or fluorine, and be is from 2 to 6, preferably 3 or 4, and ce is from 1 to 12, — preferably 1 to 6.

When B$^5$ is a group —[(CR$^{4e}_2$)$_{be}$O]$_{ce}$— wherein all the groups R$^{4e}$ are hydrogen and in all the groups [CR$^{4e}_2$)$_{be}$O] be is 2, the residues of the monomer of formula (VB) are not able to form strong secondary valence interactions with hydrophobic surfaces. Whilst residues of such monomers may be included in the polymers of the invention, it is also necessary to include residues of monomers which are capable of forming such strong secondary valence interactions if such interactions are to bind a polymer to a surface. Monomers which have groups containing oligo (higher alkylene) oxide moieties can be used to provide the necessary strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that there are more propylene oxide units than ethylene oxide units.

When B$^5$ is a group —[(CR$^{4e}_2$)$_{be}$O]$_{ce}$— then preferably be is 2 in only 50, preferably 70, more preferably 90 mole % or less of the residues —[(CR$^{4b}_2$)$_{be}$O]—.

When the group —B$^5$—R$^{12a}$ is a group capable of forming strong secondary valence interactions with a surface, then monomers containing a group (VB) may be particularly suitable for use as zwitterionic monomers containing an alkyl or fluoroalkyl group optionally containing one or more etheric oxygen atoms. Preferably, in such a case —B$^5$—R$^{12a}$ is an alkyl group optionally containing one or more etheric oxygen atoms and preferably 6 or more carbon atoms or a fluoroalkyl group optionally containing one or more etheric oxygen atoms and preferably 6 or more carbon atoms.

In one embodiment B and B$^5$ may be the same.

The groups of formula (VC) are:

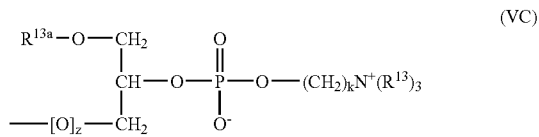

(VC)

wherein the groups R$^{13}$ are the same or different and each is hydrogen or C$_{1-4}$ alkyl, R$^{13a}$ is either (a) a group —[C(O)]$_{rs}$(CR$^{13b}_2$)$_{ss}$(SiR$^{13c}_2$) (OSiR$^{13c}_2$)$_{rr}$ R$^{13c}$ in which each group R$^{13b}$ is the same or different and is hydrogen or alkyl of 1 to 4 carbon atoms, each group R$^{13c}$ is the same or different and is alkyl of 1 to 4 carbon atoms or aralkyl, for example benzyl or phenethyl, rs is 0 or 1, ss is from 0 to 6, with the proviso that rs and ss are not both 0, and rr is from 0 to 49; or (b) a group of formula —C(O)B$^6$—R$^{13d}$, in which R$^{13a}$ is hydrogen or methyl, B$^6$ is a valence bond or a straight or branched alkylene, oxaalkylene or oligo-oxaalkylene group optionally containing one or more fluorine atoms and from 6 to 24, more preferably 6 to 18 carbon atoms and k is from 1 to 4; and if B is other than a valence bond, Z is 1 and if B is a valence bond Z is 0 if X is directly bonded to an oxygen or nitrogen atom and otherwise Z is 1.

Preferably the groups R$^{13}$ are the same. It is also preferable that at least one of the groups R$^{13}$ is methyl, and more preferable that the groups R$^{13}$ are all methyl.

Preferably k is 1 or 2, more preferably 2.

Where R$^{13a}$ is a siloxane group as defined in (a) above, each group (CR$^{13b}_2$) may be the same or different, preferably the same and preferably each group R$^{13b}$ is hydrogen. Preferably ss is from 2 to 4, and is most preferably 3 when rs is 0 or 2 when rs is 1. Each group (SiR$^{13c}_2$) may be the same, or different, preferably the same, and preferably each group R$^{13c}$ is methyl. Preferably rr is from 4 to 29.

Preferably the group R$^{13c}$ is a group —C(O)B$^6$R$^{13d}$ as defined above. In such a case, preferably B$^6$ is:

a valence bond;

an alkylene group of formula —(CR$^{3f}_2$)$_{af}$—, wherein the groups —(CR$^{3f}_2$)— are the same or different, and in each group (CR$^{3f}_2$)— the groups R$^{3f}$ are the same or different and each group R$^{3f}$ is hydrogen, fluorine or C$_{1-4}$ alkyl or fluoroalkyl, preferably hydrogen or fluorine, and is from 1 to 24, preferably 6 to 18;

an oxaalkylene group such as alkoxyalkyl having 1 to 6 carbon atoms and optionally one or more fluorine atoms in each alkyl moiety; or an oligo-oxaalkylene group of formula —[(CR$^{4f}_2$)$_{bf}$O]$_{cf}$— where the groups —(CR$^{4f}_2$)— are the same or different and in each group —(CR$^{4f}_2$)— the groups R$^{4f}$ are the same or different and each group R$^{4f}$ is hydrogen, fluorine or C$_{1-4}$ alkyl or fluoroalkyl, preferably hydrogen or fluorine, and bf is from 2 to 6, preferably 3 or 4, and cf is from 1 to 12, preferably 1 to 6.

When B$^6$ is a group —[(CR$^{4f}_2$)$_{bf}$O]$_{cf}$— wherein all the groups R$^{4f}$ are hydrogen and in all the groups [(CR$^{4c}_2$)$_{bf}$O] bf is 2, the residues of the monomer of formula (VC) are not able to form strong secondary valence interactions with hydrophobic surfaces. Whilst residues of such monomers may be included in the polymers of the invention, it is also necessary to include residues of monomers which are capable of forming such strong secondary valence interactions if such interactions are to bind a polymer to a surface. Monomers which have groups containing oligo(higher alkylene) oxide moieties can be used to provide the necessary strong secondary valence interactions, so can monomers which contain oligo alkylene oxide moieties in which at least 50, preferably 70, more preferably 90 mol % of individual alkylene oxide units contain 3 or more carbon atoms. Thus, for instance a mixed oligo(ethylene oxide/propylene oxide) side chain could be used provided that these are more propylene oxide units then ethylene oxide units.

When $B^6$ is a group $—[(CR^{4f}_2)_{bf}O]_{cf}—$ then preferably bf is 2 in only 50, preferably 70, more preferably 90 mol % or less of the residues $—[(CR^{4f}_2)_{bf}O]—$.

When the group $—B^6—R^{13a}—$ is a group capable of forming strong secondary valence interactions with a surface, then monomers containing a group (VC) may be particularly suitable for use as zwitterionic monomers containing an alkyl or fluoroalkyl group optionally containing one or more etheric oxygen atoms. Preferably, in such a case $—B^6—R^{13a}$ is an alkyl group optionally containing one or more etheric oxygen atoms and preferably 6 or more carbon atoms or a fluoroalkyl group optionally containing one or more etheric oxygen atoms and preferably 6 or more carbon atoms.

In one embodiment B and $B^6$ may be the same.

Particular examples of preferred zwitterionic monomers are 2(methacryloyloxy)ethyl-2'(trimethylammonium)ethyl phosphate inner salt and 1[4(4'-vinylbenzyloxy)butane]-2" (trimethylammonium)ethyl phosphate inner salt.

Zwitterionic monomers, such as those of formula (II) and (III) may be prepared by conventional techniques using known reactions, for example using a suitable substituted alkyl (alk)acrylate or suitable substituted styrene as precursor. Examples of suitable substituted alkyl (alk)acrylates include dimethylaminoethyl(meth)acrylate and 2-hydroxyethyl(meth)acrylate.

Monomers of formula (II) or (III) containing a group of formula (IVB) or (IVC) may be prepared as described in Reference Example 1 to 3 or by analogous known methods.

Monomers of formula (II) or (III) containing a group of formula (IVD) in which $R^{8b}$ is $—C(O)B^1R^{8b}$ may be prepared by selective acylation of glycerophosphorylcholine or analogues thereof at the primary hydroxyl group with an activated acid derivative such as an acid anhydride $O(C(O)B^1R^{8b})_2$ or an acid halide $R^{8b}B^1COHal$ where $B^1$ and $R^{8b}$ are as defined above and Hal is halogen, followed by acylation of the secondary hydroxyl group with an appropriate acylating agent, for example methacryloyl chloride. Purification, for example by column chromatography on a suitable support, may be performed after each acylation or after the second acylation only. Suitable activated acid derivatives include acid anhydrides, acid halides, reactive esters and imidazolides. The acylations may be performed in a suitable anhydrous, aprotic solvent, for example N,N— dimethylformamide, optionally in the presence of a suitable non-nucleophilic base, for example triethylamine.

Alternatively, the primary alcohol group in glycerophosphoryl choline or an analogue thereof may be blocked by reaction with a suitable protecting group reagent, for example t-butyldimethylsilyl chloride, under standard conditions and the secondary hydroxy group then treated with an acylating agent such as methacryloyl chloride. The t-butyldimethylsilyl protecting group may be removed by treatment with a dilute organic or mineral acid, for example p-toluene sulphonic acid, hydrochloric acid or with tetrabutylammonium fluoride. The deblocked primary hydroxyl group may then be treated with an activated acid derivative such as an acid anhydride $O(C(O)B^1R^{8b})_2$ or acid halide $R^{8b}B^1COHal$ where $B^1$ and $R^{8b}$ are as defined above, and Hal is halogen.

Analogues of glycerophosphorylcholine (compounds of formula (II) or (III) containing a group (IVD) where $R^{8a}$ is hydrogen) may be prepared by reaction of phosphorus oxychloride with a bromoalcohol in an inert aprotic solvent, such as dichloromethane, to give a bromoalkylphosphorodichloridate. The dichloro derivative thus produced may then be treated with an appropriately protected glycerol derivative, for example 2,2-dimethyl 1,3-dioxolane-4-methanol, in the presence of a base, for example triethylamine, followed by acid hydrolysis to give a bromoalkylphosphoroglycerol derivative. This may then be treated with an amine $NR^8_3$, where $R^8$ is as defined above, for example trimethylamine, to generate the glycerophosphorylcholine analogue. This preparation is depicted in the following scheme.

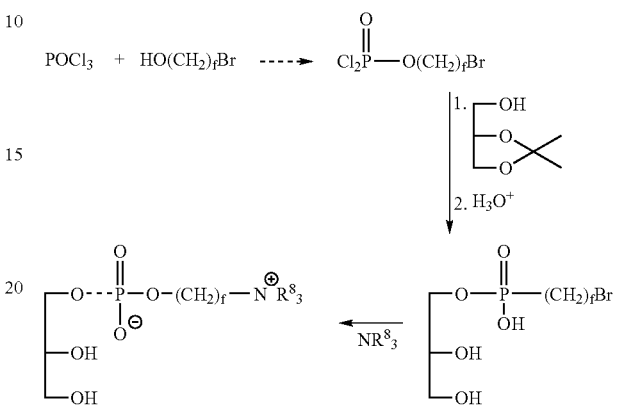

where $R^8$ and f are as defined in relation to groups of formula (IVD).

Monomers of formula (II) or (III) containing a group of formula (IVE) in which $R^{9a}$ is $—C(O)B^2R^{9b}$ may be prepared by the selective acylation of glycerophosphorylcholine or an analogue thereof at the primary hydroxyl group with for example, methacryloyl chloride followed by reaction at the secondary hydroxyl group using an activated acid derivative, such as an acid halide $O(C(O)B^2R^{9b})_2$ or an acid halide $R^{9b}B^2COHal$, where $B^2$ and $R^{9b}$ are as defined above and Hal is halogen. The intermediates and final products may be purified, as necessary using column chromatography. Optionally, protecting group strategy, similar to that outlined above in relation to production of monomers containing a group of formula (IVD) may be employed.

Monomers of formula (II) or (III) containing a group of formula (IVF) may be prepared in an analogous manner to monomers containing groups of formula (IVD) or (IVE).

Monomers of formula (II) or (III) containing a group of formula (VB) or (VC) may be prepared by direct analogy with methods described for monomers containing groups of formula (IVD), (IVE) and (IVF) respectively.

Comonomers Capable of Stably Binding a Polymer to a Surface

The polymer of the invention comprises residues of comonomer containing a group capable of stably binding a polymer at a surface which is a group capable of forming covalent bonds with a coreactive group at the surface and/or cross-linking the polymer as well as the residues of the comonomer containing a zwitterionic group. Optionally, where the monomer containing a zwitterionic group also contains a group capable of stably binding the polymer to a surface, further groups capable of stably binding to a surface may be provided by additional comonomer residues containing a group capable of binding the polymer to a surface.

As has already been mentioned, the nature of the group capable of binding to a surface, and therefore the nature of the comonomers containing such groups, will depend upon the nature of the surface which is to be coated with the polymer. The various types of such comonomers will now be described.

It will be appreciated that in some circumstances it may be desirable to use a combination of different comonomers containing groups capable of binding to a surface. Preferably a comonomer of type a), b) and/or c) as defined below or a combination of such comonomers is used, more preferably a comonomer of types b) is used with a comonomer of a) or c).

a) Comonomers Containing an Alkyl, Fluoroalkyl or Siloxane Group

The comonomers containing an alkyl, fluoroalkyl or siloxane group, which are suitable for providing binding to a hydrophobic surface, are comonomers containing an alkyl group of 6 or more carbon atoms which group optionally contains one or more etheric oxygen atoms and optionally one or more carbon-carbon double or triple bonds or a fluoroalkyl group, preferably of 6 or more carbon atoms, which group optionally contains one or more etheric oxygen atoms and optionally one or more carbon-carbon double or triple bonds, or containing a siloxane group, containing up to 50 silicon atoms, preferably in a linear chain.

Preferably the alkyl or fluoroalkyl groups contains up to 24 carbon atoms, for instance up to 18 carbon atoms, or containing a siloxane group, containing up to 50 silicon, preferably in a linear chain. Preferred comonomers containing an alkyl, fluoroalkyl or siloxane group are those of general formula (VI)

$$Y^1—Q \qquad (VI)$$

where $Y^1$ is an ethylenically unsaturated polymerisable group selected from

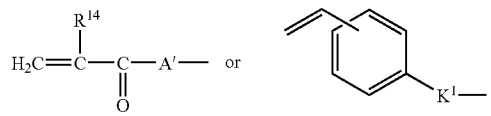

where $R^{14}$ is hydrogen or $C_1$–$C_4$ alkyl,

A' is —O— or —$NR^{15}$— where $R^{15}$ is hydrogen or a $C_1$–$C_4$ alkyl group or $R^{15}$ is a group Q;

$K^1$ is a group —$(CH_2)_l$OC(O)—, —$(CH)_lC(O)O$—, —$(CH_2)_lOC(O)O$—, —$(CH_2)_lNR^{16}$—, —$(CH_2)_lNR^{16}C(O)$—, —$(CH_2)_lC(O)NR^{16}$—, —$(CH_2)_lNR^{16}C(O)O$—, —$(CH_2)_lOC(O)NR^{16}$—, —$(CH_2)_lNR^{16}C(O)NR^{16}$— (in which the groups $R^{16}$ are the same or different), —$(CH_2)_l$O—, —$(CH_2)_lSO_4$—, a valence bond and l is from 1 to 12 and $R^{16}$ is hydrogen or a $C_1$–$C_4$ alkyl group; and Q is (a) a straight or branched alkyl, alkoxyalkyl or (oligo-alkoxy)alkyl chain containing 6 or more, preferably 6 to 24, carbon atoms unsubstituted or substituted by one or more fluorine atoms and optionally containing one or more carbon-carbon double or triple bonds; or (b) a siloxane group —$(CR^{16a}_2)_{qq}(SiR^{16b}_2)(OSiR^{16b}_2)_{PR}R^{16b}$ in which each group $R^{16a}$ is the same or different and is hydrogen or alkyl of 1 to 4 carbon atoms or aralkyl, for example benzyl or phenethyl, each group $R^{16b}$ is alkyl of 1 to 4 carbon atoms, qq is from 1 to 6 and pp is from 0 to 49.

Preferred comonomers of formula (VI) bearing a group Q include those of formula (VII) and (VIII):

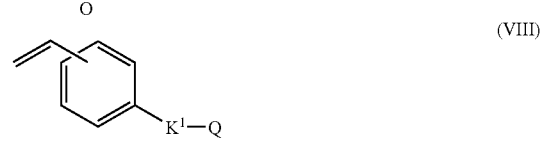

wherein:

$R^{14}$, A', $K^1$ and Q are as defined in relation to formula (VI).

Preferably in the compounds of formula (VII) $R^{14}$ is hydrogen methyl or ethyl, more preferably methyl so that the compound of formula (VII) is preferably an acrylic acid, methacrylic acid or methacrylic acid derivative.

In the compounds of formula (VIII) $K^1$ may for instance be a valence bond. Where $K^1$ is a group then preferably l is from 1 to 6, more preferably 1, 2 or 3 and most preferably l is 1. When $K^1$ is a group —$(CH_2)_lNR^{16}$—, —$(CH_2)_lOC(O)NR^{16}$—, —$(CH_2)_lNR^{16}C(O)O$—, —$(CH_2)_lNR^{16}C(O)$—, —$(CH_2)_lC(O)NR^{16}$— or —$(CH_2)_lNR^{16}C(O)NR^{16}$— then $R^{16}$ is preferably hydrogen, methyl or ethyl, more preferably hydrogen.

In the compounds of formula (VIII), preferably the vinyl group is para to the group —$K^1$—Q.

Preferably Q is an alkyl or fluoroalkyl group optional] containing one or more etheric oxygen atoms and optionally or more carbon-carbon double or triple bonds.

More preferably Q is:

an alkyl group of formula —$(CR^{17}_2)_mCR^{17}_3$ wherein the groups —$(CR^{17}_2)$— are the same or different, and in each group —$(CR^{17}_2)$—the groups $R^{17}$ are the same or different and each group $R^{17}$ is hydrogen, fluorine or $C_{1-4}$ alkyl or fluoroalkyl and m is from 5 to 23 if Q contains no fluorine atoms or from 1 to 23, preferably 5 to 23, if Q contains one or more fluorine atoms;

an alkoxyalkyl having 1 to 12 carbon atoms in each alkyl moiety; unsubstituted or substituted by one or more fluorine atoms; or an (oligo-alkoxyl) alkyl group of formula —$[(CR^{18}_2)_nO]_o(CR^{18}_2)_nR^{18}$ where the groups —$(CR^{18}_2)$— are the same or different and in each group —$(CR^{18}_2)$— the groups $R^{18}$ are the same or different and each group $R^{18}$ is hydrogen, fluorine or $C_{1-4}$ alkyl or fluoroalkyl and n is from 2 to 6, preferably 3 to 4, and 0 is from 1 to 12.

When Q is a group —$[(CR^{18}_2)_nO]_o(CR^{18}_2)_nR^{18}$ wherein all the groups $R^{18}$ are hydrogen and in all the groups —$[(CR^{18}_2)_nO]$— n is 2 the group of formula Q is not able to form strong secondary valence interactions with hydrophobic surfaces. Whilst residues of monomers containing such a group may be included in the polymers of the invention, it is also necessary to include residues of monomers which are capable of forming such strong secondary valence interactions if such interactions are to bind a polymer to a surface. Monomers which have groups containing oligo (higher alkylene) oxide moieties can be used to provide monomers which contain oligo-alkylene oxide moieties in which at least 50 mol % of individual alkylene oxide units contain 3 or more carbons atoms. Thus, for instance a mixed oligo(ethylene oxide/propylene oxide) side chain could be used provided that there are more propylene oxide units than ethylene oxide units.

Where Q is an (oligo-alkoxy)-alkyl group containing residues —[(CR$^{18}_2$)$_n$O]— wherein n is 2, then preferably n is 2 in no more than 50 mol % of the residues —[(CR$^{18}_2$)$_n$O]—.

Alternatively, Q may be a group in which one or more of the alkyl or alkylene moieties in such an alkyl, alkoxyalkyl or (oligoalkoxy) alkyl group is replaced by a corresponding alkenyl, alkynyl, alkenylene or alkynylene moiety.

Preferred groups Q include alkyl, alkoxyalkyl and (oligoalkoxy)alkyl groups optionally containing one or more carbon-carbon double or triple bonds of 8 or more, more preferably 10 or more, even more preferably 12 or more, for instance 14 or more, such as 16 or more carbon atoms. Such groups may contain one or more fluorine atoms and be therefore fluoroalkyl derivatives. Preferably however, such groups do not contain any fluorine atoms.

Particularly preferred groups are straight chain alkyl or fluoroalkyl groups optionally containing one or more carbon-carbon double or triple bonds.

Where Q is a siloxane group, each group —(CR$^{16a}_2$)— may be the same or different, preferably the same, and preferably each group R$^{16a}$ is hydrogen. Preferably qq is from 2 to 4, and is most preferably 3. Each group —(SiR$^{16a}_2$)— may be the same or different, preferably the same, and preferably each group R$^{16a}$ is methyl. Preferably pp is from 4 to 29. Preferred comonomers where Q is a siloxane group are those of formula (VII).

In one specific embodiment the group Q does not contain any ethylenic unsaturation, i.e. any carbon-carbon double or triple bonds.

Particular examples of comonomers containing an alkyl, fluoroalkyl or siloxane group include: n-dodecyl methacrylate, octadecyl methacrylate, hexadecyl methacrylate, 1H,1H,2H,2H-heptadecafluorodecyl methacrylate, p-octyl styrene, p-dodecyl styrene and monomethacryloxypropyl terminated siloxanes. n-Dodecyl methacrylate is particularly preferred.

Comonomers containing a physisorbable alkyl or fluoroalkyl, which does not contain a carbon-carbon double or triple bond, or a siloxane group such as those of formulae (VII) and (VIII) are commercially available or may be, prepared by conventional techniques using known reactions.

In a second specific embodiment of such comonomers, the group Q does contain ethylene unsaturation, i.e. one or more carbon-carbon double or triple bonds. Such comonomers may for example contain a vinylic, divinylic, acetylenic or diacetylenic moiety. Comonomers containing acetylenic rather than vinylic unsaturation are in general preferred, especially those containing a single acetylenic group.

Comonomers which contain such an ethylenic unsaturated group are capable of providing crosslinking between linear polymer claims once the polymer is coated onto a substrate, as well as binding to the substrate by physisorption. Such crosslinking may improve the stability of the coating and is typically formed by irradiation, for example with uv— or gamma-radiation. The crosslinking of such groups may be employed either alone or in addition to the use of a comonomer containing a reactive group as a crosslinkable comonomer as described below.

Particularly preferred crosslinkable comonomers capable of binding to a substrate by physisorption are those of formula (VIIA) and (VIIIA).

CH$_2$=CR$^{14}$—C(O)—A'—QQ (VIIA)

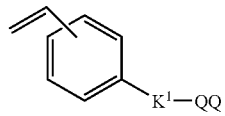
(VIIIA)

in which R$^{14}$, A' and K$^1$ are as hereinbefore defined and QQ is an alkynyl group containing 6 or more carbon atoms and one or two, preferably one, carbon-carbon triple bonds provided that the acetylenic moieties are not directly bonded to A' or K$^1$.

The present invention provides, as a further feature, comonomers of formula (VIIA) and (VIIIA).

Amongst such comonomers it is preferred that QQ is an alkynyl group containing from 6 to 24 carbon atoms, preferably 8 or more, more preferably 10 or more, even more preferably 12 or more, for instance 14 or more, such as 16 or more carbon atoms.

It is also preferred that the group QQ does not contain a terminal acetylenic moiety, i.e. a group —C≡CH.

A particularly preferred group QQ is 7-dodecynyl and a specific example of a compound of formula (VIIA) containing such a group is dodec-7-yn-1-ol methacrylate.

The compound of formula (VIIA) and (VIIIA) and other comonomers of formula (VII) and (VIII) containing an ethylenically unsaturated physisorbable group Q, may be prepared by anology with known methods. Their preparation is illustrated by Reference Example 2.

b) Comonomers Bearing a Reactive Group

Preferred comonomers, which are suitable for providing binding to a hydrophillic surface having functional groups, contain a reactive group capable of covalently binding to a 2S surface and are of general formula (IX)

Y$^2$—Q$^1$ (IX)

where Y$^2$ is an ethylenically unsaturated polymerisable group selected from

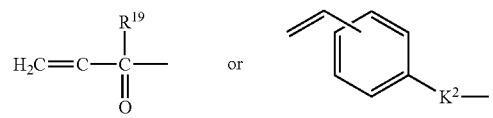

where R$^{19}$ is hydrogen or C$_1$–C$_4$ alkyl,

K$^2$ is a group —(CH$_2$)$_q$OC(O)—, —(CH)$_q$C(O)O—, —(CH$_2$)$_q$OC(O)O—, —(CH$_2$)$_q$NR$^{20}$—, —(CH$_2$)$_q$NR$^{20}$C(O)—, —(CH$_2$)$_q$C(O)NR$^{20}$—, —(CH$_2$)$_q$NR$^{20}$C(O)O—, —(CH$_2$)$_q$OC(O)NR$^{20}$—, —(CH$_2$)$_q$NR$^{20}$C(O)NR$^{20}$— (in which the groups R$^{20}$ are the same or different), —(CH$_2$)$_q$O—, or —(CH$_2$)$_q$SO$_3$—, or a valence bond and q is from 1 to 12 and R$^{20}$ is hydrogen or a C$_1$–C$_4$ alkyl group; and Q$^1$ is a reactive group capable of reacting to provide covalent binding to a surface.

Preferred comonomers of formula (IX) bearing a reactive group Q$^1$ include those of formula (X) and (XI) defined below.

The compounds of formula (X) are:

$$\begin{array}{c} R^{19} \\ | \\ CH_2=C \\ | \\ C-Q^2 \\ \| \\ O \end{array} \quad (X)$$

wherein:

$R^{19}$ is as defined with reference to formula (X), and $Q^2$ is a reactive group.

Preferably in the compounds of formula (X) $R^{19}$ is hydrogen, methyl or ethyl, more preferably methyl, so that the compound of formula (X) is preferably an acrylic acid, methacrylic acid or ethacrylic acid derivative.

Preferably $Q^2$ is hydrogen, or more preferably —OH or a group of the formula:

—T—B$^7$—Q$^3$ where T is —O—, or —NR$^{21}$— where $R^{21}$ is hydrogen, $C_1$-$C_4$ alkyl or a group —B$^7$—Q$^3$;

B$^7$ is a valence bond or, more preferably, a straight or branched alkylene, oxaalkylene or oligo-oxaalkylene chain; and $Q^3$ is a reactive group capable of reacting to provide covalent binding to a surface such as an aldehyde group or a silane or siloxane group containing one or more reactive substituents such as halogen, for example chlorine, or alkoxy, generally containing from 1 to 4 carbon atoms, for example methoxy or ethoxy, or, more preferably $Q^3$ is a hydroxyl, amino, carboxyl, epoxy, —CHOHCH$_2$Hal, (in which Hal is a halogen atom such as chlorine, bromine or iodine) succinimido, tosylate such as 2(N-methylpyridinium) tosylate, triflate, imidazole carbonyl-amino, or an optionally substituted triazine group. $Q^3$ can also be cinnamyl; ethylenically and acetylenically unsaturated groups; acetoacetoxy; methylol; and chloroalkylsulphone groups; acetoxy; mesylate; carbonyl di(cycloalkyl carbodiimidoyl; and oximino.

Preferably B$^7$ is:

an alkylene group of formula —(CR$^{22}_2$)$_r$—, wherein the groups —(CR$^{22}_2$)— are the same or different, and in each group —(CR$^{22}_2$)— the groups R$^{22}$ are the same or different and each group $R^{22}$ is hydrogen or $C_{1-4}$ alkyl, preferably hydrogen, and r is from 1 to 12, preferably 1 to 6;

an oxaalkylene group such as alkoxyalkyl having 1 to 6 carbon atoms in each alkyl moiety; or an oligo-oxaalkylene group of formula —[(CR$^{23}_2$)$_s$O]$_t$(CR$^{23}_2$)$_3$— where the groups —(CR$^{23}_2$)— are the same or different and in each group —(CR$^{23}_2$)— the groups $R^{23}$ are the same or different and each group $R^{23}$ is hydrogen or $C_{1-4}$ alkyl, preferably hydrogen, and s is from 1 to 6, preferably 2 or 3, and t is from 1 to 11, preferably 1 to 5.

Preferred groups B$^7$ include alkylene, oxaalkylene and oligo-oxaalkylene groups of up to 12 carbon atoms.

Where $Q^3$ is a silane or siloxy group, preferably B$^7$ is an alkylene group of 1 to 6, preferably 2 to 4, more preferably 3 s carbon atoms.

Particular examples of the group B$^7$ are —CH$_2$—, —CH$_2$CH$_2$— and —(CH$_2$)$_6$—.

The compounds of formula (XI) are:

$$\text{(XI)}$$

wherein $K^2$, $B^7$ and $Q^3$ are as defined in relation to formula (IX),

In the compounds of formula (XI) preferably the vinyl group is para to the group —K$^2$—B$^7$—Q$^3$.

$K^2$ may for instance be a valence bond. Where $K^2$ is a group then preferably q is from 1 to 6, more preferably 1, 2 or 3 and most preferably q is 1. When $K^2$ is a group —(CH$_2$)$_q$NR$^{20}$—, —(CH$_2$)$_q$OC(O)NR$^{20}$, —(CH$_2$)$_q$NR$^{20}$C(O)O—, —(CH$_2$)$_q$NR$^{20}$C(O)—, —(CH), C(O)NR$^{20}$— or —(CH$_2$)$_q$NR$^{20}$C(O)NR$^{20}$— then $R^{20}$ is preferably hydrogen, methyl or ethyl, more preferably hydrogen.

Particular examples of comonomers bearing a reactive group include chloromethylstyrene, methacrylic acid, 2-aminoethylmethacrylate, 2,3-epoxypropyl methacrylate, 3-chloro-2-hydroxypropylmethacrylate, 2-methacryloyloxy-ethyl dichlorotriazine, 3-chloro-2-hydroxy-propylmethacrylamide and glycidyl methacrylate and reactive methacrylate esters containing the group HetC(O)O— in which (Het) is a heterocyclic ring, for example benzotriazole or imidazole and reactive methacrylate esters containing a group R$^{16}$OC(O)— in which $R^{16}$ is a succinimido or pentafluorophenyl group.

Particularly preferred comonomers bearing reactive groups are 2-aminoethyl-methacrylate and 3-chloro-2-hydroxypropylmethacrylate.

Comonomers bearing a reactive group capable of binding covalently to a surface, such as those of formula (X) or (XI), are commercially available or may be prepared by conventional techniques using known reactions.

Comonomers of formula (X), which are dichlorotriazine monomers may be prepared in known manner for example by reacting a substituted hydroxy-alkyl(alk)acrylate or aminoalkyl(alk)acrylate with trichlorotriazine in a suitable solvent and in the presence of a base.

Comonomers of formula (XI) which are reactive methacrylate esters in which the ester groups contains an imidazole group may be prepared in known manner by reacting a substituted hydroxyalkyl(alk)acrylate (e.g. 2-hydroxyethyl (meth)acrylate), polyethylene-oxide(meth)acrylate or polypropyleneoxide (meth)acrylate with 1,1-carbonyl-diimidazole in a dry solvent. Analogous known methods may be used to prepare succinimido and pentafluorophenyl methacrylate-esters of formula (X), by reaction with a reactive ester, acid halide or acid anhydride.

Where comonomers containing a reactive group are used to bind a copolymer to a surface by covalent bonding, it will be appreciated that not all of the reactive groups need necessarily bind to surface reactive groups and that groups not so bound may participate in other chemistry. Such groups may in particular provide points for the attachment of moieties such as ligands to the polymer, when coated onto a substrate.

Comonomers containing a reactive group, such as compounds of formula (X) and (XI) may be used as comonomers containing crosslinkable groups, which react with other crosslinkable groups, rather than a monomer which bind covalently to a surface.

Where comonomers containing a reactive group are used to provide such crosslinkable groups then the crosslinkable groups and/or the copolymerisation conditions will be chosen so that they will not crosslink when the comonomers are copolymerised; thus the polymerisation product will be an uncrosslinked linear copolymer which may be subsequently crosslinked after coating the copolymer onto a surface so as to improve the stability of the coating. When such crosslinking between linear polymer chains is employed the crosslinkage may be formed either between two such crosslinkable groups or between a crosslinkable group and a non-inert group in a diluent comonomer residue (defined later). Such a crosslinkage may be formed either by direct reaction of the groups forming the crosslinkage or by reaction of these groups with a reactive bridging molelcule for example a reactive gas, such as ammonia.

Residues of such comonomers may therefore be present in polymers which are designed to coat hydrophobic surfaces and containing residues of a zwitterionic monomer and a comonomer containing an alkyl, fluoroalkyl or siloxane group, which is of formula (VII) or (VIII). Similarly residues of such comonomers may also be present in polymers designed to bind to a surface by ionic interaction and which contains residues of a compound of formula (XIII) or (XIV) as defined below.

Preferred reactive comonomers which are used to crosslink the comonomer, rather than provide covalent binding to the surface, are those of formula (X) or (XI) in which $Q^2$, or $Q^4$ contains a crosslinkable cinnamyl, epoxy, —CHOHCH$_2$Hal (in which Hal is a halogen atom), methylol, silyl, an ethylenically unsaturated crosslinkable group, such as an acetylenic, diacetylenic, vinylic or divinylic group, or an acetoacetoxy or chloroalkyl sulfone, preferably chloroethyl sulphone, group.

Particular examples of comonomers bearing a group capable of crosslinking include methacrolein, cinnamyl methacrylate, 2,3-epoxypropyl methacrylate, 3-chloro-2-hydroxypropyl methacrylate, hydroxymethyl methacrylamide, 3-(trimethoxysilyl)propyl methacrylate, 2-acetoacetoxyethyl methacrylate, 3-(vinylbenzyl)-2-chloroethyl sulfone.

When a polymer of the invention, containing crosslinkable groups, is coated on a substrate the polymer is in substantially uncrosslinked form. After coating, crosslinking of crosslinkable groups may be performed to increase the strength and stability of the polymer coating.

c) Comonomers Bearing an Ionic Group

Preferred comonomers bearing an ionic group capable of binding to a surface by ionic interaction are of general formula (XII)

$$Y^4—B^9—Q^5 \quad \text{(XII)}$$

where $Y^4$ is an ethylenically unsaturated polymerisable group selected from

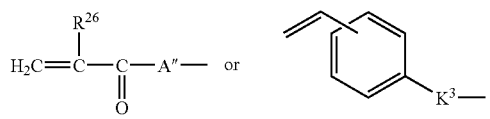

where $R^{26}$ is hydrogen or $C_1$–$C_4$ alkyl;

A" is —O— or —NR$^{27}$—, wherein $R^{27}$ is hydrogen or a $C_1$–$C_4$ alkyl group or $R^{27}$ is a group —B$^9$—Q$^5$;

B$^9$ is a valence bond, a straight or branched alkylene, oxaalkylene or oligo-oxaalkylene group;

K$^3$ is a group —(CH$_2$)$_x$OC(O)—, —(CH)$_x$C(O)O—, —(CH$_2$)$_x$OC(O)O—, —(CH$_2$)$_x$NR$^{28}$—, —(CH$_2$)$_x$NR$^{28}$C(O)—, —(CH$_2$)$_x$C(O)NR$^{28}$—, —(CH$_2$)$_x$NR$^{28}$C(O)O—, —(CH$_2$)$_x$OC(O)NR$^{28}$—, —(CH$_2$)$_x$NR$^{28}$C(O)NR$^{28}$— (in which the groups R$^{28}$ are the same or different), —(CH$_2$)$_x$O—, —(CH$_2$)$_x$SO$_4$—, a valence bond (optionally in combination with B$^9$) and x is from 1 to 12 and R$^{28}$ is hydrogen or a $C_1$–$C_4$ alkyl group;

$Q^5$ is an ionic group capable of binding to a surface by ionic interaction.

Preferred comonomers of formula (XII) are therefore those of formula (XIII) and (XIV):

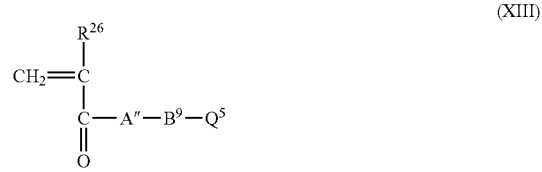

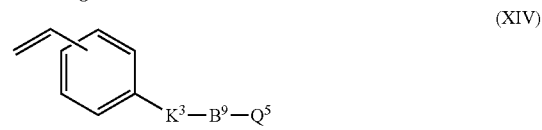

wherein:

R$^{26}$, A", B$^9$, K$^3$ and Q$^5$ are as defined in relation to formula (XII).

Preferably in the compounds of formula (XIII) R$^{26}$ is hydrogen, methyl or ethyl, more preferably methyl, so that the compound of formula (XIII) is preferably an acrylic acid, methacrylic acid or ethacrylic acid derivative.

In the compounds of formula (XIV), K$^3$ may for instance be a valence bond. Where K$^3$ is a group then x is preferably from 1 to 6, more preferably 1, 2 or 3 and most preferably x is 1. When K$^3$ is a group —(CH$_2$)$_x$NR$^{26}$—, (CH$_2$)$_x$OC(O)NR$^{26}$—, —(CH$_2$)$_x$NR$^{26}$C(O)O—, —(CH$_2$)$_x$NR$^{26}$C(O)—, —(CH$_2$)$_x$C(O)NR$^{26}$— or —(CH$_2$)$_x$NR$^{26}$C(O)NR$^{26}$— then R$^{26}$ is preferably hydrogen, methyl or ethyl, more preferably hydrogen.

In the compounds of formula (XIV) preferably the vinyl group is para to the group —K$^4$—B$^4$—Q$^4$.

Preferably B is:

an alkylene group of formula —(CR$^{29}_2$)$_y$—, wherein the groups —(CR$^{29}_2$)— are the same or different, and in each group —(CR$^{29}_2$)— the groups R$^{29}$ are the same or different and each group R$^{29}$ is hydrogen or $C_{1-4}$ alkyl, preferably hydrogen, and y is from 1 to 12, preferably 1 to 6;

an oxaalkylene group such as alkoxyalkyl having 1 to 6 carbon atoms in each alkyl moiety; or an oligo-oxaalkylene group of formula —[(CR$^{30}_2$)$_{yy}$O]$_{xx}$(CR$^{30}_2$)$_{yy}$— where the groups —(CR$^{30}_2$)— are the same or different and in each group —(CR$^{30}_2$)— the groups R$^{30}$ are the same or different and each group R$^{30}$ is hydrogen or $C_{1-4}$ alkyl, preferably hydrogen, and yy is from 1 to 6, preferably 2 or 3, and xx is from 1 to 12, preferably 1 to 6.

Preferred groups B$^9$ include alkylene, oxaalkylene and oligo-oxaalkylene groups of up to 12 carbon atoms.

Particular examples of the group B$^9$ are —CH$_2$—, —CH$_2$CH$_2$— and —(CH$_2$)$_6$—

The group Q$^5$ may be either anionic or cationic depending upon the surface to be coated. Where the surface has a cationic surface charge, the group Q$^5$ will be anionic and may for example be a carboxylate, sulphonate, hydrogen-phosphate or phosphate group. Where the surface has an anionic surface charge, the group $Q^5$ will be cationic and may for example by a group —$NR^{31}_3{}^+$, in which each group $R^{31}$ is the same or different, and is hydrogen or alkyl of 1 to 6 carbon atoms two of which groups $R^{31}$ may together from a heterocyclic ring containing from 5 to 7 atoms, preferably hydrogen or methyl, a group $N^+$Het, where Het is an unsaturated heterocyclic group such as pyridyl, substituted or unsubstituted by one or more alkyl groups of 1 to 4 carbon atoms, or a group —$PR^{32}_3{}^+$ in which each group $R^{32}$ is the same or different and is hydrogen or alkyl of 1 to 6 carbons atoms, two of which groups $R^{31}$ may together form a heterocyclic ring containing from 5 to 7 atoms, preferably methyl.

Particular examples of comonomers bearing an ionic group include acrylic acid, methacrylic acid, 2-sulfoethyl methacrylate, 2-methacryloyloxyethyl phosphate, p-styrene sulfonic acid, 2-(methacryloyloxyethyl)trimethylammonium chloride, 3-aminopropyl methacrylamide, vinylbenzyl trimethylammonium chloride.

Comonomers bearing a group capable of binding a polymer to a surface by ionic interaction, such as those of formula (XIII) and (XIV) are commercially available or may be prepared by conventional techniques using known reactions.

Diluent Comonomers

In addition to a) the residues of monomers containing a group bearing a centre of permanent positive charge or b) the residues of comonomers containing a group bearing a centre of permanent positive charge and comonomers which are capable of binding to a surface, the polymers of the present invention may comprise residues of a diluent comonomer.

Such diluent comonomers may be used to give the polymer the desired physical and mechanical properties. They may be of any known conventional radical polymerisable, preferably ethylenically unsaturated, type compatible with other comonomer(s).

Particular examples of diluent comonomers include alkyl (alk)acrylate preferably containing 1 to 4 carbon atoms in the alkyl group of the ester moiety, such as methyl (alk)acrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk)acrylamide preferably containing 1 to 4 carbon atoms in the alkyl group of the amide moiety; a hydroxyalkyl (alk)acrylate preferably containing from 1 to 4 carbon atoms in the hydroxyalkyl moiety, e.g. a 2-hydroxyethyl (alk)acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

Further diluents which may be mentioned specifically include polymerisable alkenes, preferably of 2–4 carbon atoms, eg. ethylene, dienes such as butadiene, alkylene anhydrides such as maleic anhydride and cyano-substituted alkylenes, such as acrylonitrile.

Diluent comonomers may be obtained by conventional known methods.

Of the above diluent comonomers some are inert and act simply to modify the physical and mechanical properties of copolymers containing them. Others, and in particular the hydroxyalkyl(alk)acrylates and polyhydroxyl (alk)acrylates have a reactive role in addition to simply modifying physical and mechanical properties. Such comonomers contain functional groups, such as hydroxyl groups, which may react with a crosslinking group or may react with reactive groups in other molecules to attach them to the copolymer.

It will also be appreciated that alkyl(alk)acrylates containing 6 or more carbon atoms in the alkyl group may be regarded as either diluent comonomers or comonomers capable of binding a polymer to a surface by physisorption. In particular it should be noted that a copolymer which contains such a diluent comonomer and a reactive comonomer capable of reacting at a surface to provide covalent binding to a surface may be used to coat a hydrophillic surface, the reactive comonomer providing binding to the surface and the diluent modifying physical and mechanical properties. However, such a copolymer may also be to coat hydrophobic surfaces, in which the "diluent" monomer will act as a comonomer capable of binding to the surface by physisorption and the comonomer capable of covalent binding will act as a crosslinkable comonomer.

According to a feature of the present invention polymers of the invention may be prepared by copolymerising a zwitterionic comonomer optionally a further comonomer containing a group capable of stably binding the polymer to a surface, a monomer having a reactive group and a diluent comonomer.

Any conventional technique may be used for polymerisation, typically thermal or photochemical polymerisation. Where comonomers capable of producing crosslinking in the coated polymer film are present, the polymerisation condition are set such that crosslinking does not occur during polymerisation. Thus, for example, actinic radiation would not be used to prepare a polymer containing a comonomer which can form crosslinks by exposure to actinic radiation.

For thermal polymerisation a temperature from 40 to 100° C., typically 50 to 80° C. is used. For photochemical polymerisation actinic radiation such as gamma, U.V., Visible or microwave radiation may be used. Typically U.V. radiation of wavelength 200 to 400 nm is used.

The polymerisation is generally performed in a reaction medium, which is for instance a solution or dispersion using as a solvent for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation may be carried out in the presence of one or more polymerisation initiators, such as benzoyl peroxide, 2,2'-azo-bis(2-methylpropionitrile) or benzoin methyl ether. Other polymerisation initiators which may be used are disclosed in "Polymer Handbook", 3rd edition, Ed. J. Brandrup and E. H. Immergut, Pub. Wiley-Interscience, New York, 1989.

Generally the copolymerisation is performed for 1 to 72 hours, preferably 8 to 48, for instance 16 to 24 hours, and under an inert atmosphere of for example nitrogen or argon.

The polymer is generally purified by dialysis, precipitation in a non-solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

The precise proportion and nature of the various comonomers used to prepare a copolymer according to the present invention comprising residues of a zwitterionic monomer and a comonomer containing a reactive group and optionally a further comonomer having a group capable of stably binding the polymer to a surface may be adjusted to provide a copolymer which is particularly suitable for coating a particular surface. Thus the proportion of comonomer containing a group capable of stably binding the polymer to a surface may be adapted to provide efficient physisorption at a particular hydrophobic surface, to correspond to the number of functional groups at a particular surface or to provide efficient binding by ionic interaction with a particular surface. Similarly the proportion of the zwitterionic monomer and of diluent and/or crosslinkable comonomer may be adapted to provide the desired biocompatibility and physical and mechanical properties. It will be appreciated that to obtain the desired combination of properties more than one type of zwitterionic monomer, comonomer containing a group capable of stably binding the polymer to a surface or crosslinkable and/or diluent comonomer may be used.

The monomer composition which is subjected to polymerisation to provide a polymer according to the invention comprises a minimum of 0.01%, preferably 1%, more preferably 5% by weight of zwitterionic monomer and a maximum of 99.9%, preferably 99%, more preferably 95% by weight of other monomer or monomers. Such other monomer or monomers may be a monomer or monomers containing a group capable of stably binding the polymer to a surface, a diluent monomer or monomers and/or a crosslinkable monomer or monomers.

The monomer composition further comprises a minimum of 0.01%, preferably 1%, more preferably 5% by weight of monomer or monomers containing a group capable of stably binding the polymer to a surface and a maximum of 99.9%, preferably 99%, more preferably 95% by weight of other monomer or monomers. Such other monomer or monomers may be a monomer or monomers containing a group bearing a centre of permanent positive charge, a diluent monomer or monomers and/or a crosslinkable monomer or monomers.

Where the polymer is to bind to a surface by physisorption then preferably the monomer composition comprises no more than 95%, more preferably no more than 90% and even more preferably no more than 80% by weight of monomer or monomers containing an alkyl, fluoroalkyl or siloxane group which is capable of binding the polymer to a surface by physisorption the balance of the composition being zwitterionic monomer, diluent monomer and/or crosslinkable monomer. Such a composition typically comprises up to 50% by weight of diluent comonomer or comonomers. Where diluent comonomer is present, it preferably comprises at least 1%, more preferably 5%, by weight of the total comonomer composition. Where present, crosslinkable comonomer or comonomers generally comprise from 0.1% to 20% by weight of the total comonomer composition.

Preferably the molar ratio in a copolymer containing a hydrophobic comonomer of zwitterionic monomer to comonomer containing an alkyl, fluoroalkyl or siloxane group capable of binding the polymer to a surface by physisorption is from 5:95 to 80:20, more preferably 10:90 to 50:50. In addition the copolymer preferably comprises from 5% to 50%, more preferably 10% to 25%, by mole residues of diluent monomer and/or from 0.1 to 20%, more preferably 1% to 10%, by mole residues of crosslinkable comonomer, provided that where residues of both diluent and crosslinkable comonomer are present, they do not exceed in combination 50%, preferably 35% by mole.

Where the polymer is to bind covalently to a surface then preferably the monomer composition comprises no more than 25%, more preferably up to 20% and even more preferably up to 15% by weight of monomer containing a group capable of binding the polymer to a surface covalently; the balance of the composition being zwitterionic monomer, and optionally diluent monomer or monomers. Such a composition typically comprises up to 95%, preferably to 90%, by weight of diluent comonomer or comonomers. Where diluent comonomer is present, it preferably comprises at least 5%, more preferably 10%, by weight of the total comonomer composition.

Preferably the molar ratio in the copolymer of zwitterionic monomer comonomer containing a reactive group capable of binding the polymer to a surface by covalent bonding is from 5:95 to 95:5, more preferably 50:50 to 90:10. In addition, the copolymer preferably comprises from 5% to 50%, more preferably 10% to 25%, by mole residues of diluent monomer and/or from 0.1% to 20%, more preferably 1% to 10%, by mole residues of crosslinkable comononer, provided that where residues of both diluent and crosslinkable comonomer are present, they do not exceed in combination 50%, preferably 35% by mole.

Where the polymer is to bind to a surface by ionic interaction, then preferably the molar ratio in the copolymer of zwitterionic monomer to comonomer containing an ionic group capable of binding the polymer to a surface by ionic interactions is from 5:95 to 95:5, more preferably 50:50 to 90:10. In addition, the copolymer preferably comprises from 5% to 50%, more preferably 10% to 25%, by mole residues of diluent monomer and/or from 0.1% to 20%, more preferably 1% to 10%, by mole residues of crosslinkable comonomer, provided that where residues of both diluent and crosslinkable comonomer are present, they do not exceed in combination 50%, preferably 35% by mole.

In addition the monomer composition may comprise further components such as a polymerisation initiator, chain transfer agent, acid, base, surfactant, emulsifier or catalyst of conventional type each in an amount from 0.1% to 5%, typically from 0.2% to 3% and preferably about 0.5%, by weight each relative to the total weight of the monomers.

As a further feature the present invention provides a process for biocompatibilising a surface which comprises coating the surface with a polymer according to the present invention. Various types of surfaces may be coated depending upon the nature of the groups in the polymer capable of binding it to the surface.

Polymers containing residues of monomers containing alkyl, fluoroalkyl or siloxane groups capable of binding the polymer to a surface by physisorption are particularly suitable for coating hydrophobic surfaces, e.g. polyethylene, polypropylene and polytetrafluoroethylene (PTFE) surfaces; fluorine containing polymers of the invention being particularly suited to coating PTFE surfaces.

Hydrophillic surfaces may be rendered hydrophobic and suitable for coating with such polymers by known methods (see for example "Chemical Reactions of Polymers" Ed. E. M. Fettes, 1964, Interscience, London).

Treatment with such a polymer is generally carried out by coating the surface with a solution, dispersion (including a microdispersion) of the polymer, generally in an alcoholic, aqueous, organic or halogenated solvent or a mixture thereof, e.g. methanol, ethanol, dichloromethane or freon. The treatment is generally carried out at ambient or elevated temperature, such as from 5 to 60° C.

In one specific embodiment of the invention, the copolymer is coated onto the substrate in the form of a microdispersion for example a microemulsion.

After coating the polymer may be crosslinked if it contains the residues of crosslinkable comonomer by known method for crosslinking the specific crosslinkable groups which are present. Crosslinking may, for instance, be introduced thermally, using actinic radiation, using reactive gases for example ammonia by changing the pH, using difunctional additives or by using activation chemistries for example by known methods as described in "Methods in Enzymology, volume 135, Immobilised Enzymes and Cells, part B", Ed. K. Mosbach, Academic Press Inc, New York, 1987. This activation may be performed on the dry coating, in the cases of thermal radiation or gas treatment. Alternatively for cases where the pH needs to be changed or additives need to be included, activation may be performed on the coated material in a solution which does not remove the coating.

Surfaces having functional groups such as hydroxyl, carboxyl or amino groups are particularly suitable for treatment with polymers according to the invention comprising residues of monomer containing a group capable of binding the polymer to a surface covalently.

Where necessary the surface of the substrate may be functionalised prior to treatment. For surfaces which do not have functional groups it is necessary to introduce these groups at the surface before treatment with the polymer. This can be effected by known etching or derivatising techniques, such as plasma discharge, which introduce the appropriate surface functionality (see for example "Chemical Reactions of Polymers" Ed. E. M. Fettes, 1964, Interscience, London).

In certain cases it is also necessary to activate functional groups at the surface of the substrate and/or the reactive groups of the polymer of the invention. This may be achieved by known means using a known activating agent for example a carbodiimide such as 1-ethyl-3-(3-dimethylaminopropyl)carbodiimide. Other suitable activating agents are disclosed in "Methods in Enzymology", supra. It will be appreciated that corresponding methods of activation of groups on a polymer may also be used to attach moieties, such as ligands to the polymer when coated on a substrate.

Treatment with such a polymer is generally carried out by treating the surface with a solution of the polymer, generally an alcoholic, aqueous alcoholic or aqueous solution. The treatment is generally carried out at a temperature from −5 to 50° C., for from 0.1 to 24 hours and at a pH from 2 to 13.

Surfaces having ionic groups such as carboxyl, sulphonate, phosphate, ammonium or phosphonium groups are particularly suitable for treatment with polymers according to the invention comprising residues of monomer containing a group capable of binding the polymer to ionic interaction.

Where necessary the surface of the substrate may be functionalised prior to treatment. For surfaces which do not have ionic groups it is necessary to introduce these groups at the surface before treatment with the polymer. This can be effected by known etching or derivatising techniques, such as plasma discharge, which introduce the appropriate surface functionality (see for example "Chemical Reactions of Polymers" Ed. E. M. Fettes, 1964, Interscience, London).

Treatment with such a polymer is generally carried out by treating the surface with a solution of the polymer, generally an alcoholic, aqueous alcoholic or aqueous solution. Treatment is generally carried out at a temperature from −5 to 50° C., for from 0.1 to 24 hours and at a pH from 2 to 13.

Materials may be coated with polymers of the invention by known techniques, such as dip-coating, spray-coating, web-coating or spin coating.

Materials having surfaces coated according to the present invention can be used as a construction material for implants or prostheses for the human or animal body, particularly where these implants or prostheses are to come into direct physical contact with blood and where biocompatibility and particularly haemocompatibility are required e.g. in heart valves. They can also be used in the construction of membranes and other devices that are to be brought into contact with blood or other body fluids on an extra-corporeal basis, for example in heart-lung machines or artificial kidneys.

Additionally the polymers of the invention can be used to coat materials employed in down stream processing applications e.g. separation membranes and process equipment and tubing. In particular the materials of the invention can be used to modify the surface properties of biofiltration membranes in bioreactors and fermentation systems, where the membranes come into direct contact with complex biological solutions containing e.g. proteins, polysaccharides, fats and even whole cells.. The polymers of the invention are particularly useful in reducing membrane fouling by the components of a process solution.

When the polymers of the present invention are used to coat the surface of a material which is then used in the construction coat of finished devices, it may be necessary to take precautionary steps to ensure that the coated surface is not damaged and the effectiveness of the treatment reduced before the finished device is produced.

In addition, the polymers of the present invention can be used to coat finished implants, prostheses, membranes, catheters, contact lenses, intraocular lenses, and other devices which are coated with a polymer according to the present invention to impart biocompatibility to the article.

The invention thus also provides a finished device comprising a surface having a coating thereon of a polymer of the present invention.

FIG. 1 compares scanning electron micrographs of a polyimide sheet treated and untreated with a copolymer of the invention and then contacted with blood. FIG. 1.(a) shows a scanning electron micrograph (1200×) of an unsubbed, untreated poly(imide) sheet. FIG. 1.(b) shows a scanning electron micrograph (900×) of a poly(acrylic acid) subbed poly(imide) sheet treated with poly (2(methacryloyloxyethyl)-2(trimethylammonium)ethyl phosphate-co-2-aminomethacrylate) (9:1), in accordance with Example 2.

The present invention will now be further illustrated by the following Examples:

EXAMPLES

The following assays have been used to evaluate coatings of polymers according to the present invention.

Protein Adsorption Using an Enzyme Immunoassay

The assay determines adsorption of human fibrinogen at a surface. This protein is representative of protein which is typically adsorbed at a surface. The assay can be readily modified to determine the adsorption of other proteins.

Discs (7 mm in diameter) of untreated material (as controls) and material treated with polymer as described below, were prepared and washed with phosphate buffered saline (PBS) for at least 10 minutes in the wells of microplates. The samples were incubated with human plasma (300

µl) for 10 minutes and then washed with PBS three times. Each of the test samples and each of the control samples were treated with human fibrinogen-specific antibody (300 µl) for 30 minutes and again washed with PBS three times. As a control for non-specific binding of antibody to the samples, each sample was also incubated with non-specific antibody (300 µl) for 30 minutes. A conjugate of horseradish peroxidase and a second antibody specific to the first antibody (300 µl) was added to both the test samples and the controls and incubated for 30 minutes before washing. Each of the test samples and the controls were transferred to new microplates and a solution of 2,2'-azino-bis(3-ethyl benz-thiazoline-6-sulphonic acid) (ABTS) in phosphate-citrate buffer (300 µl, 0.6 mg/ml) added, the reaction was allowed to proceed for 10 minutes. At this time an aliquot of the mixture (200 µl) was removed and added to a solution of citric acid and sodium azide in distilled water (20 µl, 0.21 g/ml and 2 mg/ml respectively). The optical density of the solutions was measured using a Techgen automated plate reader at 650 nm using the ABTS solution as blank.

In an alternative procedure, rather than using ABTS, each of the samples was transferred to wells of new microplates and a solution of o-phenylene diamine (OPD) in phosphate-citrate buffer (300 µl, 0.4 mg/ml) added, and the reaction was allowed to proceed for 10 minutes. At this time an aliquot of the mixture (200 µl) was removed from each well and the optical density of the solutions was measured using a Techgen automated plate reader at 450 nm using the OPD solution as blank.

Activated Platelet Study

Blood was collected from a healthy adult volunteer using the double syringe method where the first 5 ml of blood is discarded. The blood was collected into tri-sodium citrate (32 g/l) in the proportion of 9 volumes to 1 volume citrate in plastic tubes. The samples were kept at room temperature on a spiral mixer until used.

Discs (7 mm in diameter) of untreated material as controls and material treated with polymers as described below were prepared and placed into the wells of a microplate. The samples were incubated with whole fresh citrated blood (200 µl) on a rotary mixer for 30 minutes before washing in PBS four times. Platelet activation was measured by a proprietary assay [Lindon, J. N. et al., *Blood*, 68, 355 (1986)] and British Patent Application No. 91-25721.2].

In an alternative procedure half of the test replicates were incubated with citrated blood (200 µl) and the remainder were incubated with EDTA-treated blood on a phase shaker for 30 minutes before washing in PBS four times. Platelet activation was measured in a manner similar to that described above for detection of proteins by enzyme immunoassay using antibodies against GMP140 to detect the presence of this platelet activation marker on the surface of biomaterials. In the presence of EDTA, which extracts calcium from inside platelets, activation is inhibited, so that incubation with EDTA-treated blood acts as a non-specific control for activation, obviating the need for incubation in non-specific antibody.

Heparin Activity

Loading of Samples with Heparin

Samples of filter strips were incubated with 5 ml of a solution of heparin in PBS (usually 50 U/ml). After 30 min, the samples were rinsed for 10 sec on both sides first with PBS then with deionized water. The samples were dried on tissue paper and in air and stored at room temperature.

Preparation of Samples for Heparin Test

Heparin loaded filter strips (dip-coated or removed from whole arterial filters) were usually incubated for 5 hrs at 37° C. in PBS/BSA 1%/NaN. 0.1% to remove unstable bound heparin. The samples were then rinsed with PBS and deionized water as described and dried in air. Samples of 0.2–0.4× 0.4 cm were cut out and tested as described below.

Heparin Test

A chromogenic assay (Heparin CRS106, Sigma). The "Semi-Micro Method" described in the manual was used. Heparin loaded coated samples were placed in polystyrene test tubes. The tubes were placed into a 37° C. water bath (5 tubes). 200 µl of bovine factor Xa was added and the tubes were shaken. Following 1 min agitation, 200 µl factor Xa substrate was added to the tubes and they were agitated for 5 min. 200 µl acetic acid (>90%) was added to the tubes and the tubes were shaken. 200 µl of the solution was removed from the tubes and added to the well of a microplate (2 wells/sample) and measured at 405 nm against wells containing 200 µl of PBS. Previous results had shown that PBS gave the same absorbance reading as a reagent blank. The heparin activity was calculated with the use of a standard curve prepared with soluble heparin.

Example 1

Preparation of poly(2(methyacryloyloxyethyl)-2 (trimethyl-ammonium)ethyl phospate inner salt-co-2-aminoethyl-methacrylate) (9:1)

2(Methacryloyloxyethyl)-2(trimethylammonium)ethyl phosphate inner salt (9.96 g, 0.0335 mole) was dissolved in methanol (115 ml). Water (10 ml) was added followed by the addition of 2-aminoethylmethacrylate (0.5571 g, 0.0034 mole). The solution was stirred (250 rpm) at 22° C. under a stream of nitrogen (70 ml/min) for 30 minutes. 2,2'Azo-bis (2-methylpropionitrile) 0.12 g, 0.73 mmole) was added and the flow of nitrogen was reduced to 9 ml/min, the temperature was raised to 60° C. The temperature and nitrogen flow rate were maintained for 16 hours.

The mixture was allowed to cool and transferred to centrifuge tubes. The samples were centrifuged for 30 minutes at 4000 rpm. The samples were combined and the polymer precipitated by dropwise addition to acetone (800 ml). The acetone was decanted from the polymer and the polymer washed with acetone (200 ml). The polymer was isolated by vacuum filtration under a nitrogen atmosphere and finally dried in vacuo overnight at room temperature. IR (cm$^{-1}$; KBr disc) 3435, 2929, 2096, 1732, 1628, 1245, 1166, 1089, 970.

Example 2

Treatment of poly(acrylic acid) subbed poly(imide) sheets with poly(2(methacryloyloxyethyl)-2(trimethylammonium) ethyl phospate inner salt-co-2-aminoethylmethacrylate) (9:1)

Poly(imide) samples were placed in the plasma chamber of a plasma barrel etcher and evacuated with a pump down to a pressure of 0.001 mbar. Oxygen was then allowed to flow into the reactor. The plasma was started with 90 W forward power and nearly 0 W backward. The pressure was approximately 0.7 mbar. The plasma was turned on for 5 minutes, then the radio frequency generator (13.56 MHz) was switched off at the same time as the flow of oxygen stopped. The pressure was allowed to drop and the valve of the flask with acrylic acid was opened to let the monomer flow into the chamber (100% acrylic acid). The vacuum was decreased to 0.3 mbar. The high frequency generator was then started with 30 W forward power and 0 W backward power and the polymerisation carried out for 20 minutes. After switching off the high frequency generator and closing the valve to the acrylic acid, the chamber was evaporated again for another 5 minutes to remove all of the excess monomer.

The poly(acrylic acid) subbed poly(imide) was cut into 4×1.5 cm pieces and washed with distilled water. The squares were then added to a 1.25% solution (6.3 ml) of poly(2(methacryloyloxyethyl)-2(trimethylammonium)ethyl phosphate inner salt-co-2-aminoethylmethacrylate (9:1). 1-Ethyl-3(3-dimethylaminopropyl)carbodiimide (20 g) was then dissolved in the solution and the pH then adjusted to 5.0 using hydrochloric acid (0.5M). After 1 hour the samples were removed, washed with distilled water and allowed to dry.

Visualisation of Platelet Activation on a Surface

Blood was collected from a healthy adult volunteer using the double syringe method where the first 5 ml of blood is discarded. The blood was collected into tri-sodium citrate (32 g/l) in the proportion of 9 volumes of blood to 1 volume citrate in plastic tubes. The samples were kept at room temperature on a spiral mixer until used.

1 $cm^2$ samples of poly(2(methacryloyloxyethyl)-2-(trimethylammonium)ethyl phosphate inner salt-co-2-aminoethylmethacrylate) (9:1) coated poly(imide) as prepared above and of uncoated poly (imide) as a comparison were placed into 1 ml of the fresh citrated blood and incubated for 30 minutes on a spiral mixer at room temperature. The samples were then washed in phosphate buffered saline (PBS, pH7.4) prior to fixing in an aliquot of the following solution for 30 minutes.

2 ml 25% w/v glutaraldehyde
83 ml 0.15M PBS (pH7.4)
15 ml Saturated picric acid.

Picric acid increases the preservation of lipid-associated protein. The samples were again washed in PBS and then dehydrated using 70% and 100% methanol followed by 100% acetone prior to drying in air. Finally samples were sputter-coated with a platinum target (20 mAmps for 6×30 seconds) and observed at appropriate magnifications using a scanning electron microscope.

No platelet activation was seen on the coated poly(imide) samples whereas gross adhesion activation and aggregation were seen on the uncoated sample (see FIG. 1). The presence of the polymer on the surface was confirmed by the use of X-ray photoelectron spectroscopy (XPS). It can thus be seen that treatment of polyamide by first coating with a subbing layer of acrylic acid to render the surface reactive, and then coating with a copolymer according to the present invention substantially removed the haemostatic reaction to the polyamide.

Example 3

Preparation of poly(2(methacryloyloxyethyl)-2'(trimethylammonium)ethyl phospate inner salt-co-3-chloro-2-hydroxypropyl methacrylate (1:1)

2 (methacryloyloxyethyl) -2'(trimethylammonium)ethyl phosphate inner salt (7.46 g, 25.3 mmole), 3-chloro-2-hydroxypropyl methacrylate (4.51 g, 25.3 mmole) and p-toluene sulphonic acid monohydrate (0.1048 g, 0.55 mmole) were dissolved in methanol (101 ml). The solution was stirred (250 rpm) at 23° C. under a stream of nitrogen (50 ml/min) for 30 minutes. 2,2'-azo-bis(2-methylpropionitrile) (0.0843 g, 0.51 mmole) was added and the flow of nitrogen was reduced to 10 ml/min, the reaction temperature was raised to 60° C. This temperature and nitrogen flow rate were maintained for 16 hours.

The polymer was isolated from this mixture by precipitation in acetone (1500 ml), vacuum filtration and drying. The polymer was redissolved in methanol (40 ml) and isolated as before using acetone (1000 ml).

The resulting polymer, obtained in 62% yield was a white solid.

NMR(200 MHz, d, ppm, $CD_3OD/CDCl_3$) 4.2–4.4 (b), 4.3–4.0 (b), 3.6–3.8 (b), 3.3 (s), 1.6–2.4 (b), 1.0–1.5 (b), 0.7–1.0 (b).

IR($cm^{-1}$, KBr disc) 3416, 2959, 1727, 1655, 1490, 1247, 1165, 1088, 968, 792, 748.

Example 4

Preparation of poly(2(methacryloyloxyethyl)-2'(trimethylammonium)ethyl phospate inner salt-co-7 dodecynmethacrylate (1:2)

The polymer was prepared by a method analogous to that described in Examples 4 and 6 using 2(methacryloyloxyethyl)-2'(trimethylammonium)ethyl phosphate inner salt (8.41 g, 0.0285 mole) and n-dodecynmethacrylate (14.31 g, 0.0572 mole) dissolved 5 in propan-2-ol (160 ml) and ethyl acetate (60 ml).

The resulting polymer, obtained in 35% yield was a white powder.

NMR(100 MHz, d, ppm, $CD_3OD/CDCl_3$) 4.2–4.4(b), 3.8–4.2(b), 3.6–3.8(b), 3.3(s), 2.25(s), 1.8–2.2(b), 1.5–1.8 (b), 1.2–1.5(s), 0.8–1.0(s)

IR($cm^{-1}$, KBr disc) 3430, 2929, 2854, 1732, 1469, 1246, 1156, 108, 968, 788.

| Elemental Analysis | | | | |
|---|---|---|---|---|
| theory | C 65.1 | H 9.0 | N 1.8 | P 3.9 |
| actual | C 54.9 | H 8.5 | N 1.9 | P 4.4 |

Relative Viscosity (chloroform/ethanol 50:50, 30° C.) 1.18.

The polymer may be crosslinked by gamma-irradiation or exposure to UV light which renders the polymer insoluble in dichloromethene/methanol.

A sample of stainless steel treated with the polymer showed a reduction in protein adsorption of 68% (determined by the enzyme immunoassay described above) and a reduction in platelet activation of 100% (determined by the platelet activation assay described above, using anti GMP 140) compared to untreated material. A sample of PVC coated with the polymer showed a reduction in protein adsorption of 60% compared to untreated material as determined by the same assay technique.

Example 5

Preparation of poly(2(methacryloyloxyethyl)-2'(trimethylammonium)ethyl phospate inner salt-co-n-dodecyl methacrylate-co-2 hydroxyethylmethacrylate) (17:75:8)

The polymer was prepared by a method analogous to Examples 4 and 6, using 2(methacryloyloxyethyl)-2'(trimethylammonium)ethyl phosphate inner salt (2.0 g, 0.0068 mole), n-dodecyl methacrylate (7.65 g, 0.0301 mole) and 2 hydroxyethyl methacrylate (0.42 g, 0.0032 mole) dissolved in propan-2-ol (70 ml) and ethyl acetate (30 ml).

The resulting polymer, obtained in 53% yield was a white solid.

NMR(100 MHz, d, ppm, $CD_3OD/CDCl_3$) 4.2–4.4(b), 3.8–4.2(b), 3.6–3.8(b), 3.3(s), 1.8–2.2(b), 1.5–1.8(b), 1.2–1.5(s), 0.8–1.0(s)

IR($cm^{-1}$, KBr disc) 3435, 2925, 2860, 1729, 1468, 1243, 1152, 1089, 969, 791.

A coating solution of poly(2(methacryloyloxyethyl)-2'(trimethylammonium)ethyl phosphate inner salt-co-n-dodecyl methacrylate-co-2-hydroxyethylmetacrylate) (0.5097 g) in propan-2-ol (50 ml) was prepared. Aluminium sheet was washed with propan-2-ol, hexane and water and dried, the coating solution (0.5 ml) was applied to pieces of the aluminium sheet (7.5 cm ) by a spin coating technique using a spin speed of 1200 rpm.

Example 6

Preparation of poly(2(methacryloyloxvethvl)-2'(trimethylammonium)ethyl phospate inner salt-co-methacrylic acid (7:3)

The polymer was prepared by a method analogous to that of Examples 4 and 6 using 2(methacryloyloxyethyl)-2'(trimethylammonium)ethyl phosphate inner salt (4.44 g, 0.0149 mole), and methacrylic acid (0.54 g, 0.0063 mole) dissolved in propan-2-ol (25 ml) and water (25 ml). The polymer was isolated by precipitation in acetone (500 ml), redissolved in methanol (50 ml) and isolated by precipitation in diethyl-ether (500 ml).

The resulting polymer, obtained in 30% yield was a white solid.

NMR (100 MHz, d, ppm, $CD_3OD/CDCl_3$) 4.2–4.4(b), 3.8–4.2(b), 3.6–3.8(b), 3.3(s), 1.8–2.2(b), 1.5–1.8(b), 1.2–1.5(s), 0.8–1.0(s)

IR($cm^{-1}$, KBr disc) 3430, 2929, 2854, 1732, 1469, 1246, 1156, 1089, 968, 788

This polymer was used to treat cellulose film which had been treated with 2-aminoethyl methacrylate as follows:

A section of cellulose dialysis membrane (4×6 cm) was taken, and placed into a solution of 2-aminopropylmethacrylate (3.34 g) and ceric ammonium nitrate (0.05 g) in distilled water (20 ml). The solution was deoxygenated with N for 10 minutes, then the vessel was sealed, and left at room temperature for 2 hours. The cellulose sample was then removed from the solution, then washed extensively in distilled water for 24 hours.

The presence of amine hydrochloride moieties on the grafted sample was demonstrated by the differential uptake of anionic and cationic dyes (Trypton blue and methylene blue respectively).

Strips of the functionalised cellulose (0.5 cm×2 cm) were placed in a 10% w/w solution of the polymer in water. The samples were left to stand at room temperature for 1 hour, then washed extensively in distilled water (200 ml) for 2 hours.

Following the aqueous wash, the treated cellulose was placed into a solution of acid molybdate spray reagent and left to stand for 1 hour, then removed and washed with distilled water. The presence of phosphate groups on the sample was demonstrated by the development of a blue colour.

Example 7

Preparation of poly(2(methacryloyloxyethyl)-2'(trimethylammonium)ethyl phospate inner salt-co-n-dodecylmethacrylate-co-3-trimethoxysilylpropyl-methacrylate) and subsequent cross-linking of cast films This example illustrates the preparation of a polymer containing 3-trimethoxysilylpropylmethacrylate for subsequent cross-linking, in addition to phosphorylcholine for biocompatibility.

2(methacryloyloxyethyl)-2'(trimethylammonium)ethyl phosphate inner salt (9.6 g) was dissolved in 170 ml isopropyl alcohol and stirred over molecular sieve (4A) for 0.5 hour. The solution was then filtered into the reaction flask and 16.6 g dodecylmethacrylate and 4.6 g 3-trimethoxysilylpropylmethacrylate added along with 70 ml ethylacetate and 0.0618 g AIBN (2,2'-azo-bis(2-methylpropionitrile)). Nitrogen was bubbled through the solution for 0.5 hour and the temperature raised to 60° C. The reaction was maintained at this temperature stirring under a nitrogen atmosphere for 23 hours, after which the solution was allowed to cool and approximately half the solvent removed under reduced pressure. The polymer was isolated by precipitation into acetone and collected by filtration, drying under vacuum. Yield 17 g of a white solid. Coatings of the polymer were prepared by casting a solution of the polymer (approximately 10% w/w in methanol) containing 0.15 w/w on dry polymer of dibutyltindilaurate on glass plates and drying at 50° C. for 12 hours.

Example 8

Preparation of poly(2(methacryloyloxyethyl)-2'(trimethylammonium)ethyl phospate inner salt-co-n-dodecylmethacrylate-co-3-chloro-2 hydroxypropyl methacrylate) and biological testing of PE-coated films This example illustrates the preparation of a polymer containing 3-chloro-2 hydroxypropyl methacrylate as a cross-linking monomer in addition to phosphorylcholine for biocompatibility.

2(methacryloyloxyethyl)-2'(trimethylammonium)ethyl phosphate inner salt (69.41 g), n-dodecylmethacrylate (120.85 g), AIBN (0.3939 g) and 3-chloro-2 hydroxypropyl methacrylate (6.3 g) were dissolved in a mixture of isopropylalcohol (1380 ml)/ethyl acetate (570 ml) and the solution degassed for 0.3 hour. The reaction mixture was then stirred at 60° C. under a nitrogen atmosphere for 40 hours, allowed to cool and then precipitated into a large excess of acetone. The polymer was collected by filtration and dried.

Films of the polymer on polyethylene sheets (previously cleaned in methylated spirits) were prepared by dip coating in a solution of the polymer in ethanol (10 mg $ml^{-1}$). Cross-linking of the films was achieved by incorporation of butylammonium hydroxide in the casting solution (30 mg/200 mg of dry polymer); cross-linking was demonstrated by the failure of the films to redissolve in solvent. A fibrinogen single antibody assay showed a significant reduction in fibrinogen binding for both the uncrosslinked film and cross-linked film compared to the uncoated PE substrate.

Example 9 a) Preparation of a copolymer of HEMA-PC and allyl methacrylate 2:1

20.6 g of HEMA-PC, 4.4 g allyl methacrylate and 0.05 g AIBN were stirred in 250 cm of deoxygenated ethanol at 65° C. under a nitrogen atmosphere for 24 hours. After cooling, the solution was filtered and the solvent removed on a rotary evaporator. The resulting white powder was redissolved in dichloromethane/methanol (80/20) and precipitated in a large excess of acetone. The solid product was removed by decanting, filtered, reprecipitated again from dichloromethane/methanol and dried under reduced pressure at ambient temperature to yield approximately 20 g of a white solid which was readily soluble in ethanol and substantially free of gel. $^1$H NMR δ (D$_2$o); 5.9 (olefinic CH), 5.4 (olefinic CH$_2$), 4.1, 3.8, 3.2 (NMe$_1$), 1.9, 1.2 and 0.8. The 1H NMR spectrum was consistent with a 2:1 copolymer of HEMA-PC and allyl methacrylate with the allyl group being unreactive under the conditions of the polymerisation.

b) Coating of polydimethylsiloxane (PDMS) with MPC/AMA copolymer 25 2×1 cm3 squares of PDMS sheet (20–40 Pharmelast, SF Medical) were treated in a plasma chamber under an air atmosphere at a power of 100 W for 1 minute on each side. They were then dip coated in a 5% w/v aqueous solution of MPC/AMA (previously filtered through a 0.2 um filter) for 5 minutes, rinsed briefly with deionised water and dried overnight at ambient temperature and humidity.

Dynamic contact angle analysis (DCA) of the samples was performed using a Cahn 1a with a borate buffered saline probe solution at a stage speed of 100 μm/s. All results are quoted as average values for 5 samples. The advancing angle of the coated PDMS was 48 degrees and the receding angle was 39 degrees. For comparison, an uncoated PDMS sheet had an advancing angle of 105 and a receding angle of 59.

After cleaning with a surfactant-based contact lens cleaner (Miraflow, CIBA Vision) for 1 minute on each side, the advancing angle of the coated PDMS sheet was 53 degrees and the receding angle was 39 degrees. The minimal change in contact angle upon cleaning is evidence for a stable coating.

In previous experiments it had been shown that treatment of substrates coated with allyl methacrylate HEMA-PC copolymers resulted in additional stabilisation of the coating. Such a treatment may be advantageously applied to the products of this example.

Example 10 a) Synthesis of terpolymer of HEMA-PC:dodecyl methacrylate and 3-(trimethoxysilyl)propylmethacrylate 2:1:0.23)

HEMA-PC (9.74 g, 33 mmol) was dissolved in isopropyl alcohol (108 ml) and stirred under a blanket of nitrogen. After 20 minutes, dodecyl methacrylate (4.19 g, 16.5 mmol) and 3(trimethoxysilyl)propyl methacrylate (1.05 g, 4.2 mmol) were added in ethyl acetate (42.5 ml). Nitrogen was bubbled through the mixture for 30 minutes, AIBN (0.025 g) was added and it was heated at 65° C. for 36 hours. After cooling to room temperature the polymer was isolated by precipitation into acetone (1500 ml). The material was filtered and dried under vacuum to give the product, 13.45 g, 90% yield.

$^1$H-nmr—300.13 MHz (CDCl$_3$/CD$_3$OD). δ=0.8–1.0 (s), 1.0–1.2 (s), 1.25–1.5 (s), 1.75 (s), 3.2–3.4(s), 3.7–3.8 (s), 3.9–4.4 (m)

$^{13}$C-nmr—75.47 MHz (CDCl$_3$/CD$_3$OD). δ=1 4 (s), 18 (broad), 19 (broad), 23, 25, 26, 27, 29, 30(d), 32, 45, 46, 54, 55, 60, 64 (d), 65, 66, 67, 68

$^{32}$P-nmr—121.45 MHz (CDCl$_3$/CD$_3$OD). δ=0.4997 (s)

b) Treatment of polypropylene with polymer

An aqueous solution of sodium persulphate (10%, w/v) was taken and polypropylene pieces were added. The mixture was purged with nitrogen for 20 minutes before heating the mixture to 80° C. for two hours whilst maintaining the purging. Samples were removed and then coated by dipping in a solution of the polymer made in step a) (2 mg/ml) in ethanol. The materials were heated at 60° C. for 16 hours prior to testing.

Samples of treated polypropylene were incubated with plasma and the amount of fibrinogen determined using a single antibody ELISA assay. Coated samples were compared to untreated controls and the results are expressed in absorbance values (which are proportional to the total fibrinogen adsorbed on the surface) and as a relative percentage reduction comparing coated to uncoated samples:—

Polymer treated polypropylene, mean absorbance (n=5)= 0.068

Untreated polypropylene, mean absorbance (n=5)=1.214

Reduction in fibrinogen adsorption (Coated v uncoated)= 95%

Polypropylene strips were incubated with solutions of insulin and the amount of insulin adsorbed determined using a double antibody ELISA assay. Coated samples were compared to untreated controls and the results are expressed in absorbance values (which are proportional to the total insulin adsorbed on the surface) and as a relative percentage reduction comparing coated to uncoated samples:—

Polymer treated polypropylene, mean absorbance (n=3)= 0.105

Untreated polypropylene, mean absorbance (n=3)=0.962

Reduction in insulin adsorption (coated v uncoated)=89% c) Treatment of glass with polymer

Glass beads were pre-washed by sonication in ethanol (2×2 mins). After drying at ambient temperature, the beads were stirred for two minutes in hydrochloric acid (10M). The samples were then washed with distiled water until the washings were neutral after which they were dried in air. The beads were left in a solution of the polymer synthesised in step a) (5 mg/ml) in ethanol, removed and allowed to dry on a piece of polypropylene. The materials were heated at 60° C. for 16 hours prior to testing.

Glass beads were incubated with solutions of insulin and amount of insulin adsorbed determined using a double antibody ELISA assay. Coated samples were compared to untreated controls and the results are expressed in absorbance values (which are proportional to the total insulin adsorbed on the surface) and as a relative percentage reduction comparing coated to uncoated samples:—

Polymer treated glass, mean absorbance (n=7)=0.110

Untreated glass, mean absorbance (n=7)=0.594

Reduction in insulin adsorption (coated v uncoated)=82% d) Treatment of polymethylmethacrylate with polymer

Polymethylmethacrylate pieces were coated by dipping in a solution of a polymer synthesised as in step a) but having a slightly higher level of reactive comonomer (0.26 mole per 1 mole of dodecyl methacrylate and 2 moles HEMA-PC) (10 mg/ml) in ethanol. The materials were heated at 60° C. for 16 hours prior to testing.

Samples of treated polymethylmethacrylate were incubated with plasma and the amount of fibrinogen determined using a single antibody ELISA assay. Coated samples were compared to untreated controls and the results are expressed in absorbance values (which are proportional to the total fibrinogen adsorbed on the surface) and as a relative percentage reduction comparing coated to uncoated samples:—

Polymer treated polymethylmethacrylate, mean absorbance (n=6)=0.199

Untreated polymethylmethacrylate, mean absorbance (n=5)=2.788

Reduction in fibrinogen adsorption (Coated v uncoated)= 93%

Example 11

Quater polymers of HEMA-PC:dodecyl methacrylate:3-(trimethoxy-silyl) propyl methacrylate: 3-hydroxy propyl methacrylate (23:47:5:25)

A triple-necked round bottom flask (250 ml) was equipped with a Davis condenser, a nitrogen inlet, the, polymerisation solvent which is ethanol and a thermometer. The condenser was topped with a calcium chloride guard tube, and a magnetic follower was added to the flask. The reaction system then purged using nitrogen gas.

The HEMA-PC monomer was weighed and then stirred in the reaction solvent until dissolved. The comonomers were weighed and then stirred into the reaction solvent until dissolved. The initiator used throughout the polymer development was AIBN at a level of 2 w/w %, and this was dissolved into the reaction solvent.

The solutions were then filtered under vacuum using a buchner funnel, into the reaction vessel. The solution was degassed using a constant flow of nitrogen for a period of twenty minutes, after which time the nitrogen flow rate was reduced and the temperature increased to 62C. The polymerisation was carried out under an atmosphere of nitrogen, and maintained at 62C for When the polymerisation had finished the heat source was removed and the solution was allowed to cool to room temperature. The solvent was removed using rotary evaporation techniques until the point at which the polymer began to foam. This solution was then further diluted with dichloromethane and precipitated by dropwise addition into acetone with constant stirring. The precipitate was then collected using vacuum filtration under a blanket of nitrogen and dried at 25C in vacuo for 16 hours.

The polymer was then cooled using liquid nitrogen and ground to a fine powder using an analytical mill. The polymer was then further dried in vacuo at 25C for 16 hours. The yield of polymer obtained was recorded.

Ethanol was the reaction solvent.

The polymer product had the following properties:

| Elemental Analysis: | | | | | |
|---|---|---|---|---|---|
| | C | H | N | P | Si |
| Theoretical | 62.59 | 9.91 | 1.37 | 3.02 | 0.60 |
| Actual | 60.65 | 9.88 | 1.43 | 3.06 | 0.59 |

| Dilute Viscosity Measurements: | | | |
|---|---|---|---|
| Batch No. | Intrinsic Viscostity | Relative Viscosity | Mv |
| batch 1 | 0.1455 | 1.145 | 172769 |
| batch 2 | 0.1404 | 1.140 | 160919 |
| batch 3 | 0.1433 | 1.143 | 167718 |

Mv is Viscosity Average Molecular Weight and is expressed in Daltons.

The polymer was coated using dip coating from ethanol at 5 and 10 mg/ml.

The coating speed was 3 mm/min. The polymer was crosslinked by heating at 70C for 4 hours or longer eg overnight.

The polymer was then used to coat a number of steel coronary devices crosslinked by heating and submitted to a number of tests which looked at the performance of the hydrogel coating during in vitro testing.

All of the SEM microscopy was carried out using a Hitachi S4000 field emission SEM. The samples were prepared by mounting on the stubs using conductive graphite pads. Sputter coating was not used.

Molecular weight, radius of gyration and second virial coefficients for the polymers were calculated from Zimm plots obtained through the use of static light scattering. The measurements were made using a PL-LSP light scattering photometer starting at 30 and increasing in 15 increments. The polymers were measured in ethanol with toluene used as the reference. A refractometer was used to establish the dn/dc value for the solutions.

Molecular weights for the polymer was found to be in the region of 200,000 daltons, with a radius of gyration of 14 nm.

The biological performance (fibrinogen adsorption) of the crosslinkable polymers has been shown to be good. The adsorption value was about 0.2 (comparative unit relating to absorbance in an ELISA test) for the PC polymer and about 1.8 for the uncoated steel.

An important property required of the final polymer coating is its mechanical stability. The angioplasty devices undergo several deformations and stresses when deployed, as such any coating must respond to these conditions. This is demonstrated in experiments, where coronary stents were coated with the quater polymer and a more brittle coating not containing the hydroxypropyl methacrylate monomer. The more brittle polymer coating ruptures under the stresses associated with balloon expansion. This is not the case when stents coated with the new polymer are subjected to the procedure.

Example 12

Preparation of poly(2-(Methacryloyloxyethyl)-2'-(Trimethylammoniumethyl) phospate, inner salt)-co-(n-Dodecyl methacrylate)-co-(2-(Methacryloyloxy) ethyl trimethyl ammonium chloride)-co-(3-Trimethyoxysilylpropyl methacrylate) 30:60:6:4 terpolymers

12.1 Monomer Feed Synthesis

The zwitterionic monomer (40.68 g, 0.138 mole) and cationic monomer (5.73 g, 0.0275 mole) were weighed in a glove box environment dried by $P_2O_5$. Dodecyl methacrylate (69.45 g, 0.273 mole), trimethoxysilyl monomer (4.53 g, 0.0182 mole) and α-azo-isobutyronitrile (AIBN) initiator (1.202 g, 1%) were weighed in air. A 3 neck reaction flask, fitted with water condenser, nitrogen gas flow and monomer feed tubing, and primed with anhydrous n-propanol (60 g) solvent, was immersed in a heated 90° C. oil bath. The monomers and initiator were dissolved in 300 g of n-propanol solvent and magnetically stirred in a measuring cylinder sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2.25 hours. The reaction was stirred for another hour. A second charge of AIBN initiator (0.12 g), dissolved in 3 ml n-propanol, was added and the reaction mixture was stirred for a further 50 min, taking the total reaction time to 4 hours.

Once cooled to room temperature, the reaction mixture was filtered through a sintered glass filter. The solvent was removed at 40° C.–50° C. by rotary evaporator to give a white foam residue that was later redissolved in 480 ml dichloromethane and 40 ml methanol solvent mixture and dropwise precipitated into 4000 ml acetone. A white solid product settled from the acetone leaving a slightly cloudy supernatant. The product was separated by Buchner flask and 113 Whatman wet strenghtened filter paper, and dried in a room temperature vacuum oven for up to 24 hours prior to a second workup and precipitation in acetone. The product was weighed (82.9 g) to provide a 68.9 wt % yield, bottled in a brown glass vial and refridgerated.

Characterisation of Product

The polymer requires by weight C, 63.08%; H, 10.13%; P, 3.55%; N, 1.93%; Si, 0.43%; Cl, 0.81%; found C, 58.1% H 9.98% P, 3.09% N, 1.90% Si, 0.20%, $^1$Hnmr (400 MHz, ppm, $CD_3OD:CDCl_3$ 1:1 v:v) 4.34, 4.30, 3.98, 3.72, 3.38, 3.29, 3.22, 1.67, 1.32, 0.92, 0.10. Specific viscosity of 10 mg/ml solution in ethanol:chloroform (1:1 v:v) is 0.13. The polymer product was subjected to the chloride ion assay to establish the rate of inclusion of cationic monomer; required 4.76 wt %, found 4.82 wt % and 4.94 wt %.

12.2 One Pot Synthesis

Zwitterionic monomer (4.87 g, $1.65 \times 10^{-2}$ mole), dodecyl methacrylate (8.11 g, $3.19 \times 10^{-2}$ mole), cationic monomer (0.67 g, $0.32 \times 10^{-2}$ mole) and trimethoxy-silyl monomer (0.53 g, $0.21 \times 10^{-2}$ mole) were rinsed into the reaction vessel with 114 ml solvent mixture of 15:85 v/v % MeOH:EtOH. Anhydrous cationic monomer was predissolved in 3 ml pure MeOH before being rinsed into the reaction vessel. Dodecyl methacrylate monomer was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g) being rinsed into the reaction mixture with 2 ml solvent mixture. The reaction was magnetically stirred and maintained up a positive pressure nitrogen blanket sufficient to bubble through a mineral oil bubbler. The reaction time was 39 hours.

Once cooled to room temperature, the reaction mixture appeared clear with a slight haze. The solvent was removed at room temperature by rotary evaporator to give a white foam residue that was later redissolved in 50 ml dichloromethane and added dropwise into vigorously stirred 500 ml acetone. A white solid product settled from the acetone leaving a slightly cloudy supernatant. The product was separated by Buchner flask and 113 Whatman wet strengthened filter paper, and dried in a room temperature vacuum oven for up to 72 hours. The product was weighed to provide a 91 wt % yield, bottled in a glass jar and refrigerated.

Characterisation

The polymer requires by weight C, 62.93%; H, 10.11%; P, 3.61%; N, 1.95%; Si, 0.42% Cl, 0.80%; found C, 57.88%; H, 10.20%; P, 3.30%; N, 1.84%; Si, 0.12% Cl, 0.78%. $^1$Hnmr (400 MHz, ppm, $CD_3OD:CDCl_3$ 1:1 v:v) 4.33, 4.29, 3.97, 3.71, 3.38, 3.34, 3.29, 3.22, 1.67, 1.32, 0.92, 0.09; specific viscosity in a 10 mg/ml solution of ethanol:chloroform (1:1) is 0.32.

Example 13

Preparation of poly(2-Methacryloyloxyethyl)-2'-(Trimethylammoniumethyl) phospate, inner salt)-co-n-Dodecyl methacrylate)-co-(2-Methacryloyoxy) ethyl trimethyl ammonium chloride)-co-(hydroxy propyl methacrylate)-co-(3-Trimethoxysilylpropyl methacrylate) 23:47:6:20:4 polymers

13.1 Monomer Feed Synthesis

Zwitterionic monomer (34.10 g, 0.116 mole) and cationic monomer (6.3 g, 0.030 mole) were weighed in a glove box environment dried by $P_2O_5$. Dodecyl methacrylate (60.01 g, 0.236 mole), hydroxypropyl methacrylate monomer (14.51 g, 0.101 mole), trimethoxysilyl monomer (5.00 g, 0.020 mole) and AIBN initiator (0.2409 g, 0.2%) were weighed in air. A 3 neck reaction flask, fitted with water condenser, nitrogen gas flow and monomer feed tubing, and primed with anhydrous n-propanol:isopropyl acetate (60:40 mass ratio) solvent, was immersed in a heated 90° C. oil bath. The monomers and initiator were dissolved in n-propanol:isopropyl acetate solvent and magnetically stirred in a measuring cylinder_sealed with parafilm. The reaction mixture was drawn into polypropylene tubing placed inside the measuring cylinder and through silicone tubing via a peristaltic pump to enter the heated reaction vessel in a dropwise process. A complete transfer to the heated vessel took 2 hours. The reaction was stirred for another hour. A second charge of AIBN initiator (0.0241 g, 0.02 wt %) was added and the reaction mixture was stirred for a further hour, taking the total reaction time to 4 hours. Total solids content was 30 wt % in n-propanol:isopropyl acetate (168.06 g:112.08 g).

Once cooled to room temperature, the reaction mixture was split into two batches. The first batch of reaction mixture (240 ml) was precipitated by dropwise addition to vigorously stirred methyl acetate (2000 ml). The product was separated by Buchner flask and 113 Whatman wet strengthened filter paper, and dried in a room temperature vacuum oven for up to 24 hours. The product was rapidly frozen by liquid nitrogen, milled into a fine powder and further dried in a room temperature vacuum for 24 hours. The product (50.67 g, 81.8% based on mass recovery) was bottled in a brown glass vial and stored at 4° C.

The polymer requires by weight C, 62.4%; H, 9.9%; P, 3.0%; N, 1.9%; Si, 0.4% Cl, 0.8%; found C, 57.0%; H, 9.4%; N, 1.7%; P, 2.7%. $^1$Hnmr (400 MHz, ppm, $CD_3OD$:$CDCl_3$ 1:1 v:v) 4.41, 4.08, 3.83, 3.46, 3.40, 3.34, 2.07, 1.67, 1.43, 1.18, 1.04.

The product was subjected to chloride ion assay to establish the rate of inclusion of cationic monomer: required 5.23 wt %, found 4.66 and 4.71 wt %.

13.2 One Pot Synthesis

Zwitterionic monomer (3.98 g, $1.35 \times 10^{-1}$ mole), dodecyl methacrylate monomer (7.009 g, $2.76 \times 10^{-1}$ mole), cationic monomer (0.733 g, $0.35 \times 10^{-1}$ mole), hydroxypropyl. methacrylate (1.691 g, $0.67 \times 10^{-1}$ mole) and trimethoxysilyl monomer (0.585 g, $0.24 \times 10^{-1}$ mole) were rinsed into the reaction vessel with 98 ml solvent mixture of 15:85 v:v % MeOH:EtOH. Anhydrous cationic monomer was predissolved in 3 ml pure MeOH before being rinsed into the reaction vessel. Dodecyl methacrylate was pre-columned through activated basic alumina (Brockmann 1 ca.150 mesh, 50 g) before use. Dry nitrogen gas was bubbled through for 20 minutes to degas the reaction mixture at room temperature before immersing the reaction vessel in an oil bath heated to 67° C. The vessel was heated for 15 minutes prior to AIBN initiator (0.14 g, 1.1 wt %) being rinsed into the reaction mixture with 2 ml solvent mixture. The reaction was magnetically stirred and maintained under a positive pressure nitrogen blanket sufficient to bubble through a mineral oil bubbler. The reaction time was 39.5 hours.

Once cooled to room temperature, the reaction mixture was filtered through sintered glass. The solvent was removed at <40° C. by rotary evaporator to give a white foam residue that was later redissolved in 58 ml dichloromethane and added dropwise into vigorously stirred 600 ml acetone. A white solid product settled from the acetone leaving a slightly cloudy supernatant. The product was separated by Buchner flask and 113 Whatman wet strengthened filter paper, and dried in a room temperature vacuum oven for up to 20 hours. The product was milled, further dried in a room temperature vacuum for 24 hours and weighed to provide a 93.2 wt % yield, bottled in a glass jar and refrigerated.

The polymer requires by weight C, 62.41%; H, 9.91%; P, 2.99%; N, 1.70%; Si, 0.47%; Cl, 0.89%; found C, 58.45%; H, 9.45%; P, 2.55%; N, 1.65% Si, 0.34%; Cl, 1.06%. $^1$Hnmr (400 MHz, ppm, $CD_3OD$:$CDl_3$ 1:1 v:v) 4.33, 4.29, 3.97, 3.71, 3.38, 3.34, 3.29, 3.22, 1.67, 1.32, 0.92, 0.09. Specific viscosity of 10 mg/ml solution in ethanol is 0.33. The polymer product was subjected to the chloride ion assay to establish the rate of inclusion of cationic monomer; required 5.24 wt %, found 5.16 wt % and 5.26 wt %.

13.3 Performance

The polymer was used to coat arterial filter devices. The filter was air plasma treated for 30 s prior to coating. In a separate step two dispersions were made up. The first contained 2500U heparin (bovine lung) in PBS (2.5 ml) and water (47.5 ml). The second contained 250 mg polymer in 50 ml isopropylalcohol. The two liquid compositions were mixed together then poured into the plasma treated filter which was shaken vigorously for 15 minutes to ensure contact of all the surfaces of the device with the coating mixture. The mixture was then drained out and the coated device washed three times with water. The rinsed filter was dried and placed in an oven overnight at 50° C. to ensure the reactive groups of the polymer had crosslinked.

Example 14

Performance of polymers of Examples 12 and 13

Samples of polymers of examples 12 and 13 were coated onto arterial filters from 10 mg/ml solutions in isopropanol. The filters were dip coated with the polymer solutions, which were then dried overnight. The coated polymers were kept at 70° C. overnight to ensure complete crosslinking. The filters were then tested for their fibrinogen adsorption using the performance test described above. Some samples of filter were, after coating with polymer, were loaded with heparin using the general test described above and then subjected to fibrinogen adsorption and heparin activity tests. The control was untreated filter. Table 1 shows the results for reduction in fibrinogen adsorption as compared to the control and heparin activity for the heparin loaded devices. Comparisons are quoted for two commercially available heparin coatings Medtronic CB-M40, believed to have covalently (end point attached) heparin and Medtronic M-40 believed to have ionically bound heparin, in terms of fibrinogen adsorption and heparin activity. The results show that heparin is adsorbed onto the polymer, the mechanism assumed to be an ion exchange process. The filters coated with the PC polymer have reduced fouling by fibrinogen.

TABLE 1

| Polymer of Example | Without Heparin Loading % reduction fibrinogen | With Heparin Loading | |
|---|---|---|---|
| | | % reduction fibrinogen | Heparin activity $MU/cm^2$ |
| Control | 0 | 100 | |
| 12 | 90 | 82 | 14 |
| 13 | 91 | 88 | 13 |
| comparison covalently bound Heparin | N/A | 56 | 9 |
| comparison ionically bound Heparin | N/A | 7 | <1 |

Reference Example 1

Preparation of 2 (methacryloyloxyethyl)-2'(trimethylammonium ethyl phospate inner salt The preparation is illustrated by the reaction scheme A which follows.

a) 2-Chloro-1,3-dioxapholane (1)

In a flask fitted with a pressure equalising dropping funnel, reflux condenser (fitted with a $CaCl_2$ guard tube) and magnetic stirrer, was placed a solution of phosphorus trichloride (220 ml; 346.3 g; 2.52 mol) in dichloromethane (500 ml). Ethylene glycol (139 ml; 154.7 g, 2.49 mol) was then added dropwise via the dropping funnel at such a rate that the evolution of HCl did not become too excessive. On the addition of the ethylene glycol, the condenser was arranged for distillation, and the dichloromethane removed at atmospheric pressure. When the distillate temperature reached 60° C. the flask was arranged for 5 vacuum distillation using a water pump, Distillation then gave 2-chloro-1,3-dioxaphospholane (158 ml; 224.5 g; 71.3) as a colourless mobile liquid (which fumes in moist air) b.pt. 36–40° C./21 mm Hg. [cf 45.5–47° C./20 mm Hg, Lucas et al, J. Am. Chem. Soc., 72, 5491, (1950)].

IR (cm$^{-1}$, thin film) 2980, 2905, 1470, 1210, 1005, 930, 813, 770.

b) 2-Chloro-2-oxo-1,3,2-dioxaphospholane (2)

In a flask fitted with a magnetic stirrer, reflux condenser (fitted with a CaCl$_2$ guard tube) and sintered glass gas inlet tube, was placed a solution of 2-chloro-1,3,2-dioxaphospholane (100.8 g; 0.797 mol) in dry benzene (200 ml). The solution was stirred and a steady stream of oxygen was bubbled through the solution. The reaction was mildly exothermic, and temperature control was achieved by allowing the solvent to reflux. The oxygen was passed through the reaction mixture for 6 hours. The solvent was removed by rotary evaporation, and the colourless mobile residue distilled to give 2-chloro-2-oxo-1,3,2-dioxaphospholane (2) (87.41 g; 77%) as a colourless mobile liquid -b.pt 95–97° C./0.2 mbar [c.f. 102.5–105° C./1 mbar (Edmundson, Chem. Ind. (London)), 1828 (1962); 79° C./0.4 mbar (Umeda et al., Makromol. Chem. Rapid Commun., 3, 457, (1982)].

IR(cm$^{-1}$, thin film) 2990, 2910, 1475, 1370, 1310, 1220, 1030, 930, 865, 830.

c) 2(2-Oxo-1,3,2-dioxaphospholan-2-yloxy)ethyl methacrylate (3)

In a flask fitted with a magnetic stirrer, low temperature thermometer, and a pressure equalising funnel fitted with a silica gel guard tube; was placed a solution of 2-hydroxyethylmethacrylate (20.00 g, 0.154 mol) and triethylamine (15.60 g; 0.154 mol) in dry diethyl ether (300 ml). The solution was stirred and cooled to between −20° C. and −30° C. A solution of freshly distilled 2-chloro-2-oxo-1,3,2-dioxaphospholane(2) (21.9 g; 0.154 mol) in dry diethyl ether (20 ml) was then added dropwise over 30 minutes, the temperature being held at −20° C. during the addition. Stirring was continued at this temperature for a further 1 hour and then for a further hour as the reaction mixture was allowed to warm to room temperature. The precipitated triethylamine hydrochloride was removed by filtration, and was washed well with dry ether. The ether was removed from the combined filtrate and washings by rotary evaporation. The cloudy oil residue was then shaken for 5 minutes with dry diethyl ether (50 ml) to precipitate a further crop of triethylamine hydrochloride, which was again removed by filtration. Removal of the ether on the rotary evaporator gave (3) (34.18 g; 94.3%) as a colourless viscous oil. IR (cm$^{-1}$, thin film) 1720, 1640, 1450, 1360, 1310, 1290, 1170, 1030, 930, 850.

NMR (CDCl$_3$; 60 MHz, δ ppm) 1.95 (s,3H), 4.25–4.70 (m,8H), 5.70 (m,1H), 6.25 (m,1H). Rf 0.9 (SiO$_2$, eluting with 10% methanol:90% dichloromethane; spot visualised with molybdenum blue spray reagent and with iodine vapour).

d) 2(Methacryloyloxyethyl)-2'(trimethylammonium) ethyl phospate inner salt (4).

The phospholane (3) (67.20 g; 0.285 mol) was dissolved in 100 ml of dry acetonitrile, and placed in a heavy walled tissue culture bottle. The phospholane solution was then treated with a solution of anhydrous trimethylamine (25.74 g; 0.436 mol) in dry acetonitrile (100 ml). The vessel was then sealed, and placed in a water bath held at 50° C. for 30 hours. The vessel was opened, and the solution brought to the boil. The solution was filtered whilst hot, and then set aside for crystallisation.

The product was collected by filtration, and most of the solvent removed by suction. The wet product was then washed thoroughly with anhydrous ether, then dried under reduced pressure, to give (4) as a white amorphous, hygroscopic solid (51.16 g; 61%). Evaporation of the mother liquor gave a very viscous oil (20.00 g; 23%), from which further product (4) crystallised on standing at −200° C. TLC (silica gel plates, eluting with methanol/dichloromethane (1:1 v/v)) showed one spot Rf 0.1, which was revealed with Dragendorff's reagent, Molybdenum blue spray reagent, and iodine vapour. IR(cm$^{-1}$ 1720, 1640, 1320, 1300, 1230, 1170, 970, 750.

NMR (D$_2$0; 60 MHz; δ ppm) 2.0 (s,3H), 3.27 (s,9H) 3.60–4.50 (m, 8H), 5.80, (m,1H) and 6.25 (m,1H).

CHN Found: C, 42.98%; H, 7.88%; N, 4.42%; P, 10.51%. CHN Theory: C, 44.75%; H, 7.46%; N, 4.75%; P, 10.51%.

Reference Example 2

Dodec-7-yn-1-ol Methacrylate

To dodec-7-yn-1-ol (25 g) in dichloromethane (60 ml) was added distilled triethylamine (14.1 g). The mixture was cooled in an ice bath (0.5° C.) and stirred as distilled methacryloyl chloride (16.2 g) in dichloromethane (50 ml) was added over 10 minutes. The temperature of the reaction was allowed to warm to ambient and the mixture stirred for two hours. Water (150 ml) was added and the organic layer was removed and successively extracted with water (2×150 ml) and saturated sodium bicarbonate solution (2×150 ml), washed with brine (150 ml) and dried over anhydrous sodium sulphate. The solvent was removed under reduced pressure to give a pale yellow oily liquid which was distilled under reduced pressure (0.18 mBar, 106–110° C.) in the presence of copper (1) chloride to give dodec-7-yn-1-ol methacrylate, 17 g, 50% yield.

$^1$H-NMR (200 MHz,d,ppm,CDCl$_3$): 0.90 (t,3H), 1.45 (m,10H), 1.70 (m,2H), 1.95 (s,3H), 2.15 (m,6H), 4.15 (t,2H), 5.55 (s,1H), 6.10 (s,1H).

Reaction Scheme A

Step (a)

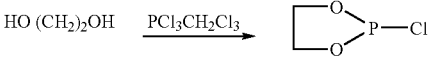

Step (b)

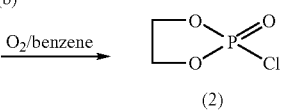

Step (c)

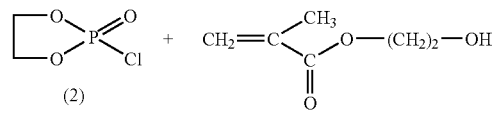

49

-continued

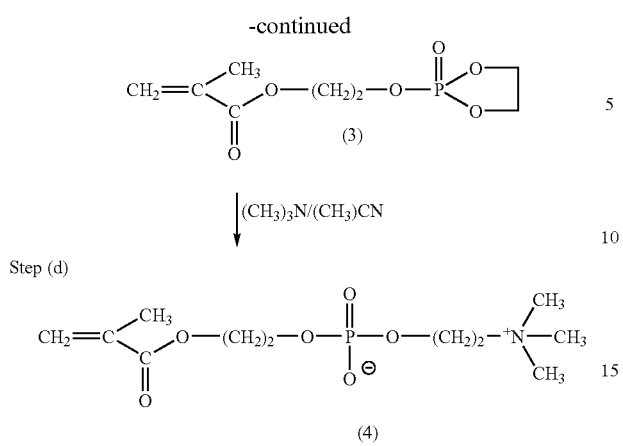

Steps (a) to (d) correspond with the steps in Reference Example 1.

Reaction Scheme B

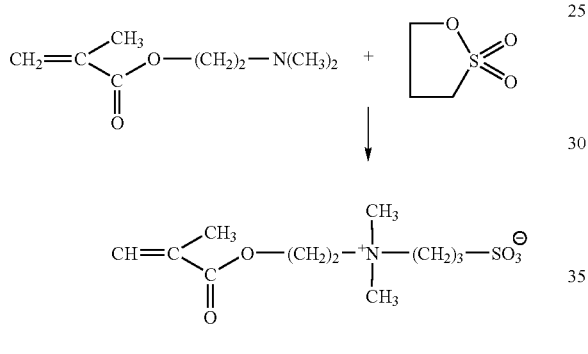

Reaction Scheme C

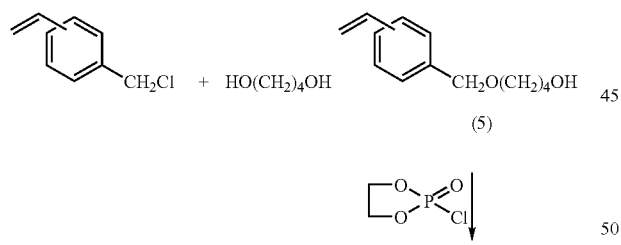

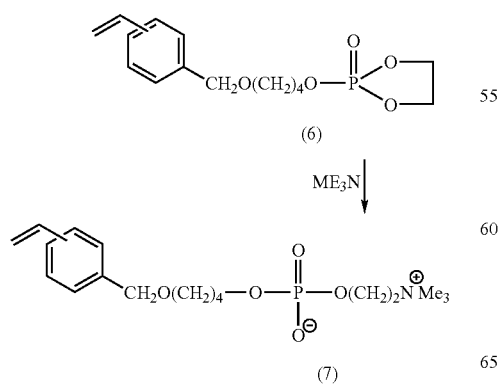

50

What is claimed is:
1. A cross-linked polymer formed by
a) radical polymerisation of radical polymerisable monomers including
   i) a zwitterionic monomer having the formula:

Y—B—X wherein
B is a straight or branched alkylene, oxaalkylene or oligo-oxaalkylene chain optionally containing one or more fluorine atoms up to and including perfluorinated chains, or if X contains a carbon-carbon chain between B and the centre of permanent position charge or if Y contains a terminal carbon atom bonded to B, a valence bond;
X is a zwitterionic group selected from groups, IVC, IVD and IVF in which group IVC has the formula

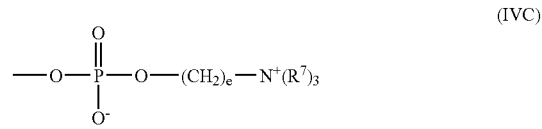 (IVC)

where
the groups $R^7$ are the same or different and each is hydrogen or $C_{1-4}$ alkyl, and e is from 1 to 4;
group IVD has the formula

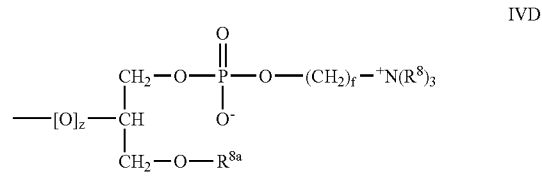 IVD wherein
the groups $R^8$ are the same or different and each is hydrogen or $C_{1-4}$ alkyl, $R^{8a}$ is hydrogen or a group —C(O)$B^1R^{8b}$ wherein $R^{8b}$ is hydrogen or methyl, $B^1$ is a valence bond or straight or branched alkylene, oxaalkylene or olig-oxaalkyene group, and f is from 1 to 4; and if B is other than a valence bond z is 1 and if b is a valence bond z is 0, if X is directly bonded to an oxygen or nitrogen atom and otherwise z is 1;
group IVE has the formula

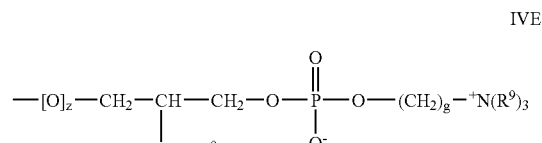 IVE wherein
the groups $R^9$ are the same or different and each is hydrogen or $C_1$–$C_4$ alkyl, $R^{9a}$ is hydrogen or a group —C(O)$B^2R^{9b}$, wherein $R^{9b}$ is hydrogen or methyl, $B^2$ is a valence bond or a straight or branched alkylene, oxaalkylene or oligo-oxaalkylene or oligo-oxaalkylene group, and g is from 1 to 4; and if B is other than a valence bond z is 1 and if B is a valence bond z is 0 if X is directly bonded to an oxygen or nitrogen atom and otherwise z is 1; and group IVF has the formula

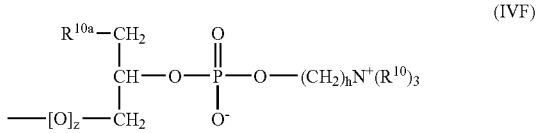

wherein the groups $R^{10}$ are the same or different and each is hydrogen or $C_{1-4}$ alkyl, $R^{10a}$ is hydrogen or a group $-C(O)B^3R^{10b}$ wherein $R^{10b}$ is hydrogen or methyl, $B^3$ is a valence bond or a straight or branched alkylene, oxaalkylene or oligo-oxaalkylene group, and h is from 1 to 4; and if B is other than a valence bond z is 1 and if B is a valence bond z is 0 if X is directly bonded to the oxygen or nitrogen and otherwise z is 1 and;

Y is an ethylenically unsaturated polymerisable group selected from

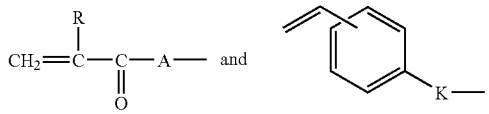

wherein:

R is hydrogen or a $C_1$–$C_4$ alkyl group;

A is —O— or —$NR^1$ where $R^1$ is hydrogen or a $C_1$–$C_4$ alkyl group or $R^1$ is —B—X where B and X are as defined above; and $K^2$ is a group —$(CH_2)_pOC(O)$—, —$(CH_2)_pC(O)O$—, —$(CH_2)_pOC(O)O$—, —$(CH_2)_pNR^2$—, —$(CH_2)_p$ $NR^2C(O)$—, —$(CH_2)_pC(O)NR^2$—, —$(CH_2)_pNR^2C$ (O)—, —$(CH_2)_pOC(O)NR^2$—, —$(CH_2)_pNR^2C(O)$ $NR^2$—, (in which the groups $R^2$ are the same or different) —$(CH_2)_pO$, —$(CH_2)_pSO_3$—, or, optionally in combination with B, a valence bond and p is from 1 to 12 and $R^2$ is hydrogen or a $C_1$–$C_4$ alkyl group and ii) a monomer having a reactive group of the formula general formula (XII)

$$Y^2—B^7—Q^3 \qquad (XII)$$

where $Y^2$ is an ethylenically unsaturated polymerisable group selected from

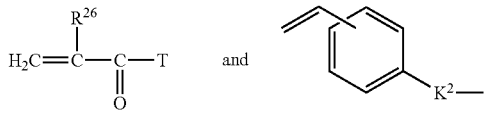

where $R^{26}$ is hydrogen or $C_1$–$C_4$ alkyl;

T is —O— or $NR^{27}$ or , wherein $R^{27}$ is hydrogen or a $C_1$–$C_4$ alkyl group or $R^{27}$ is a —$B^7Q_3$ group;

$B^7$ is a valence bond a straight or branched alkylene oxaalkylene or oligo-oxaalkylene group;

$K^2$ is a group —$(CH_2)_qOC(O)$—, —$(CH_2)_qC(O)O$—, —$(CH_2)_qOC(O)O$—, —$(CH_2)_qNR^{20}$—, —$(CH_2)_q$ $NR^{20}C(O)O$—, —$(CH_2)_qC(O)NR^{20}$—, —$(CH_2)_q$ $NR^{20}C(O)O$—, —$(CH_2)_qOC(O)NR^{20}$—, —$(CH_2)_q$ $NR^{20}C(O)NR^{20}$—(in which the groups $R^{20}$ are the same or different), —$(CH_2)_qO$— or —$(CH_2)_qSO_3$— or, or a valence bond and q is from 1 to 12 and $R^{20}$ is hydrogen or $C_1$–$C_4$ alkyl group; and $Q^3$ is a reactive group selected from the groups consisting of aldehyde groups; silane and siloxane groups containing one or more substituents selected from halogen atoms and $C_{1-4}$-alkoxy groups; hydroxyl; amino; carboxyl; epoxy; —$CHOHCH_2Hal$ (in which Hal is selected from chlorine, bromine and iodine atoms); succinimido; tosylate; triflate; imidazole carbonylamino; optionally substituted triazine groups; cinnamyl; ethylenically and acetylenically unsaturated groups; acetoacetoxy; methylol; and chloroalkylsulphone groups; and b) cross-linking the polymer by forming cross-linkages between groups $Q^3$ derived from the said monomer having a reactive group.

2. A polymer according to claim 1 in which $Q^3$ is selected from the group consisting of aldehyde, silane and siloxane groups containing one or more substituents selected from halogen atoms and $C_{1-4}$ alkoxy groups, amino, epoxy, $CHOHCH_2Hal$ (in which Hal is halogen), succinimido, tosylate, triflate, imidazolecarbonyl amino and optionally substituted triazine groups.

3. A polymer according to claim 1 in which the group $Q^3$ is selected from the group consisting of amino, acetylenically unsaturated hydrocarbon groups, 3-chloro-2-hydroxypropyl and 3-trimethyoxy silyl propyl.

4. A polymer according to claim 1 in which the said monomer having a reactive group is selected from the group consisting of 2-aminoethylmethacrylate, 7-dodecynmethacrylate, 3-chloro-2- hydroxypropylmethacrylate and 3-(trimethoxysilyl) propylmethacrylate.

5. A polymer according to claim 1 in which said radical polymerisable monomers include a comonomer having the general formula (VI)

$$Y^1—Q \qquad (VI)$$

where $Y^1$ is an ethylenically unsaturated polymerisable group selected from

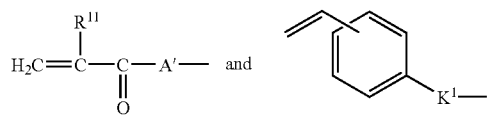

where $R^{14}$ is hydrogen or $C_1$–$C_4$ alkyl,

A' is —O— or —$NR^{15}$— where $R^{15}$ is hydrogen or a $C_1$–$C_4$ alkyl group or $R^{15}$ is a group Q;

$K^1$ is a group —$(CH_2)_lOC(O)$—, —$(CH_2)_lC(O)O$—, —$(CH_2)_lOC(O)O$—, —$(CH_2)_lNR^{16}$, —$(CH_2)_lNR^{16}C$ (O)—, —$(CH_2)_lC(O)NR^{16}$—, —$(CH_2)_lNR^{16}CH(O)$ O—, —$(CH_2)_lOC(O)NR^{16}$—, —$(CH_2)_lNR^{16}C(O)$ $NR^{16}$—(in which the groups $R^{16}$ are the same or different), —$(CH_2)_lO$—, —$(CH_2)_lSO_3$, a valence bond and l is from 1 to 12 and $R^{16}$ is hydrogen or a $C_1$–$C_4$ alkyl group; and Q is selected from the group consisting of straight and branched alkyl, alkoxyalkyl and (oligo-alkoxy)alkyl groups containing 6 to 24 carbon atom, any of which groups is unsubstituted or substituted by one or more fluorine atoms and optionally contains one or more carbon-carbon double or triple bonds; and siloxane groups $(CR^{16a}_2)_{qq}(SiR^{16}_2)(OSiR^{16b}_2)_{pp}R^{16b}$ in which each group $R^{16a}$ is the same or different and is selected from the group consisting of hydrogen, alkyl groups of 1 to 4 carbon atoms and aralkyl groups, each group $R^{16b}$ is alkyl of 1 to 4 carbon atoms, qq is from 1 to 6 and pp is from 0 to 49.

6. A polymer according to claim 5 in which $Y^1$ is

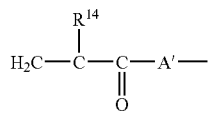

in which $R^{14}$ is methyl;

A' is —O—; and

Q is an alkyl group of the formula $-(CR^{17}_2)_m CR^{17}$ wherein the groups $-(CR^{17})-$ are the same or different and in each group $-(CR^{17}_2)-$ the groups $R^{17}$ are the same or different and each group $R^{17}$ is selected from the group consisting of hydrogen, $C_{1-4}$-alkyl and -fluoroalkyl and fluorine and m is in the range 5 to 23.

7. A polymer according to claim 6 in which the said comonomer is selected from the group consisting of n-dodecyl methacrylate, octadecyl methacrylate, hexadecylmethacrylate, 1H, 1H, 2H, 2H-heptadecafluorodecylmethacrylate, p-octyl styrene, p-dodecyl styrene and monomethacryloyloxypropyl terminated siloxanes.

8. A polymer according to claim 7 in which the said comonomer is dodecyl methacrylate.

9. A polymer according to claim 1 in which the said radical polymerisable monomers include a diluent monomer selected from the group consisting of $C_{1-4}$-alkyl(alk)acrylates, N, N-dialkylamino alkyl(alk)acrylates containing 1 to 4 carbon atoms in each N-alkyl group and 1 to 4 carbon atoms in the alkylene group, $C_{1-4}$ alkyl(alk)acrylamide, hydroxy $C_{1-4}$-alkyl(alk)acrylate, N-vinyl lactam having 5–7 atoms in the lactam ring, styrene, derivatives of styrene having ring substituents selected from $C_{1-4}$ alkyl groups and halogen atoms, polyhydroxyl (alk)acrylates, alkenes, butadiene, maleic anhydride and acrylonitrile.

10. A polymer according to claim 9 in which the diluent monomer is selected from hydroxy $C_{1-4}$-alkyl(alk)acrylates and polyhydroxyl(alk)acrylates.

11. A polymer according to claim 1 in which the said radical polymerisable monomers include at least 5% by weight zwitterionic monomer and at least 0.1% by weight monomer having a reactive group.

12. A polymer according to claim 1 in which the said radical polymerisable monomers include at least 5% by weight zwitterionic monomer and 0.1% to 20% by weight monomer having a reactive group.

13. A polymer according to claim 9 in which the said radical zwitterionic monomers include at least 5% by weight, at least 0.1% by weight monomer having a reactive group and 5 to 20% by weight diluent monomer.

14. A polymer according to claim 5 in which the said radical polymerisable monomers include at least 5% by weight zwitterionic monomer, at least 0.1% by weight monomer having a reactive group and 5 to 90% by weight of said comonomer.

15. A polymer according to claim 1 in which said cross-linkage is by direct reaction of groups $Q^3$ with one another.

16. A polymer according to claim 1 in which said cross-linkage is by reaction of groups $Q^3$ with a reactive bridging molecule.

17. A process in which a cross-linkable polymer is cross-linked by forming cross-linkages between reactive groups $Q^5$ on the polymer wherein the cross-linkable polymer is formed by a) radical polymerisation of radical polymerisable monomers including i) a zwitterionic monomer having the formula:

Y—B—X wherein

B is a straight or branched alkylene, oxaalkylene or oligo-oxaalkylene chain optionally containing one or more fluorine atoms up to and including perfluorinated chains, or if X contains a carbon-carbon chain between B and the centre of permanent position charge or if Y contains a terminal carbon atom bonded to B, a valence bond;

X is a zwitterionic group selected from groups, IVC, IVD and IVF in which group IVC has the formula

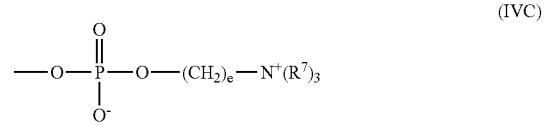

where the groups $R^7$ are the same or different and each is hydrogen or $C_{1-4}$ alkyl, and e is from 1 to 4;

group IVD has the formula

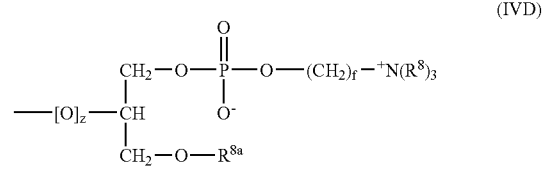

wherein the groups $R^8$ are the same or different and each is hydrogen or $C_{1-4}$ alkyl, $R^{8a}$ is hydrogen or a group $-C(O)B^1 R^{8b}$ wherein $R^{8b}$ is hydrogen or methyl, $B^1$ is a valence bond or straight or branched alkylene, oxaalkylene or olig-oxaalkyene group, and f is from 1 to 4; and if B is other than a valence bond z is 1 and if b is a valence bond z is 0, if X is directly bonded to an oxygen or nitrogen atom and otherwise z is 1;

group IVE has the formula

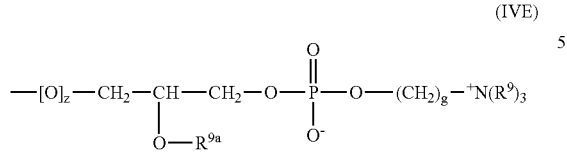
(IVE)

wherein
the groups $R^9$ are the same or different and each is hydrogen or $C_1$–$C_4$ alkyl, $R^{9a}$ is hydrogen or a group —C(O)$B^2R^{9b}$, wherein $R^{9b}$ is hydrogen or methyl, $B^2$ is a valence bond or a straight or branched alkylene, oxaalkylene or oligo-oxaalkylene or oligo-oxaalkylene group, and g is from 1 to 4; and if B is other than a valence bond z is 1 and if B is a valence bond z is 0 if X is directly bonded to an oxygen or nitrogen atom and otherwise z is 1; and group IVF has the formula

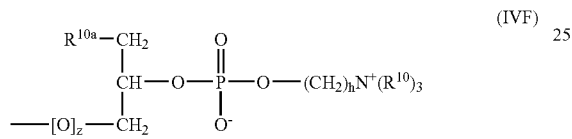
(IVF)

wherein
the groups $R^{10}$ are the same or different and each is hydrogen or $C_{1-4}$ alkyl, $R^{10a}$ is hydrogen or a group —C(O)$B^3R^{10b}$ wherein $R^{10b}$ is hydrogen or methyl, $B^3$ is a valence bond or a straight or branched alkylene, oxaalkylene or oligo-oxaalkylene group, and h is from 1 to 4; and if B is other than a valence bond z is 1 and if B is a valence bond z is 0 if X is directly bonded to the oxygen or nitrogen and otherwise z is 1 and;

Y is an ethylenically unsaturated polymerisable group selected from

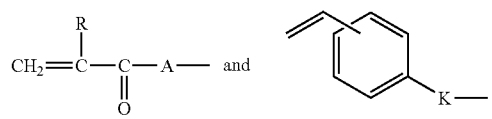

wherein:
R is hydrogen or a $C_1$–$C_4$ alkyl group;
A is —O— or —$NR^1$ where $R^1$ is hydrogen or a $C_1$–$C_4$ alkyl group or $R^1$ is —B—X where B and X are as defined above; and
$K^2$ is a group —$(CH_2)_pOC(O)$—, —$(CH_2)_pC(O)O$—, —$(CH_2)_pOC(O)O$—, —$(CH_2)_pNR^2$—, —$(CH_2)_pNR^2C(O)$—, —$(CH_2)_pC(O)NR^2$—, —$(CH_2)_pNR^2C(O)$—, —$(CH_2)_pOC(O)NR^2$—, —$(CH_2)_pNR^2C(O)NR^2$—, (in which the groups $R^2$ are the same or different) —$(CH_2)_pO$, —$(CH_2)_pSO_3$—, or, optionally in combination with B, a valence bond and p is from 1 to 12 and $R^2$ is hydrogen or a $C_1$–$C_4$ alkyl group and ii) a monomer having a reactive group of the formula general formula (XII)

$Y^2$—$B^7$—$Q^3$ (XII)

where
$Y^2$ is an ethylenically unsaturated polymerisable group selected from

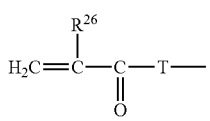 and 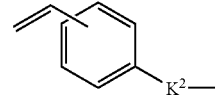

where
$R^{26}$ is hydrogen or $C_1$–$C_4$ alkyl;
T is —O— or $NR^{27}$ or , wherein $R^{27}$ is hydrogen or a $C_1$–$C_4$ alkyl group or $R^{27}$ is a —$B^7Q_3$ group;
$B^7$ is a valence bond a straight or branched alkylene oxaalkylene or oligo-oxaalkylene group;
$K^2$ is a group —$(CH_2)_qOC(O)$—, —$(CH_2)_qC(O)O$—, —$(CH_2)_qOC(O)O$—, —$(CH_2)_qNR^{20}$—, —$(CH_2)_qNR^{20}C(O)O$—, —$(CH_2)_qC(O)NR^{20}$—, —$(CH_2)_qNR^{20}C(O)$—, —$(CH_2)_qOC(O)NR^{20}$—, —$(CH_2)_qNR^{20}C(O)NR^{20}$—(in which the groups $R^{20}$ are the same or different), —$(CH_2)_qO$— or —$(CH_2)_qSO_3$— or, or a valence bond and q is from 1 to 12 and $R^{20}$ is hydrogen or $C_1$–$C_4$ alkyl group; and $Q^3$ is a reactive group selected from the groups consisting of aldehyde groups; silane and siloxane groups containing one or more substituents selected from halogen atoms and $C_{1-4}$-alkoxy groups; hydroxyl; amino; carboxyl; epoxy; —$CHOHCH_2Hal$ (in which Hal is selected from chlorine, bromine and iodine atoms); succinimido; tosylate; triflate; imidazole carbonylamino; optionally substituted triazine groups; cinnamyl; ethylenically and acetylenically unsaturated groups; acetoacetoxy; methylol; and chloroalkylsulphone groups.

18. A process according to claim 17 in which $Q^3$ is selected from the group consisting of aldehyde, silane and siloxane groups containing one or more substituents selected from halogen atoms and $C_{1-4}$ alkoxy groups, amino, epoxy, $CHOHCH_2Hal$ (in which Hal is halogen), succinimido, tosylate, triflate, imidazolecarbonyl amino and optionally substituted triazine groups.

19. A process according to claim 17 in which the group $Q^3$ is selected from the group consisting of amino, acetylenically unsaturated hydrocarbon groups, 3-chloro-2-hydroxypropyl and 3-trimethyoxy silyl propyl.

20. A process according to claim 17 in which the said monomer having a reactive group is selected from the group consisting of 2-aminoethylmethacrylate, 7-dodecynmethacrylate, 3-chloro-2-hydroxypropylmethacrylate and 3-(trimethoxysilyl) propylmethacrylate.

21. A process according claim 17 in which said radical polymerisable monomers include a comonomer having the general formula (VI):

$Y^1$—Q (VI)

where
$Y^1$ is an ethylenically unsaturated polymerisable group selected from

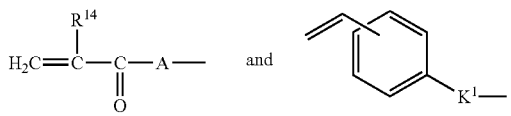

and where
R$^{14}$ is hydrogen or C$_1$–C$_4$ alkyl,
A' is —O— or —NR$^{15}$— where R$^{15}$ is hydrogen or a C$_1$–C$_4$ alkyl group or R$^{15}$ is a group Q;
K$^1$ is a group —(CH$_2$)$_l$OC(O)—, —(CH$_2$)$_l$C(O)O—, —(CH$_2$)$_l$OC(O)O—, —(CH$_2$)$_l$NR$^{16}$—, —(CH$_2$)$_l$NR$^{16}$C(O)—, —(CH$_2$)$_l$C(O)NR$^{16}$—, —(CH$_2$)$_l$NR$^{16}$CH(O)O—, —(CH$_2$)$_l$OC(O)NR$^{16}$—, —(CH$_2$)$_l$NR$^{16}$C(O)NR$^{16}$—(in which the groups R$^{16}$ are the same or different), —(CH$_2$)$_l$O—, —(CH$_2$)$_l$SO$_3$, a valence bond and l is from 1 to 12 and R$^{16}$ is hydrogen or a C$_1$–C$_4$ alkyl group; and
Q is selected from the group consisting of straight and branched alkyl, alkoxyalkyl and (oligo-alkoxy)alkyl groups containing 6 to 24 carbon atom, any of which groups is unsubstituted or substituted by one or more fluorine atoms and optionally contains one or more carbon-carbon double or triple bonds; and siloxane groups (CR$^{16a}$$_2$)$_{qq}$(SiR$^{16b}$$_2$)(OSiR$^{16b}$$_2$)$_{pp}$R$^{16b}$ in which each group R$^{16a}$ is the same or different and is selected from the group consisting of hydrogen, alkyl groups of 1 to 4 carbon atoms and aralkyl groups, each group R$^{16b}$ is alkyl of 1 to 4 carbon atoms, qq is from 1 to 6 and pp is from 0 to 49.

22. A polymer according to claim 17 in which Y$^1$ is

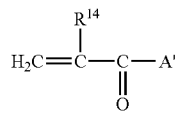

in which
R$^{14}$ is methyl;
A' is —O—; and
Q is an alkyl group of the formula —(CR$^{17}$$_2$)$_m$CR$^{17}$ wherein the groups —(CR$^{17}$)— are the same or different and in each group —(CR$^{17}$$_2$)— the groups R$^{17}$ are the same or different and each group R$^{17}$ is selected from the group consisting of hydrogen, C$_{1-4}$-alkyl and -fluoroalkyl and fluorine and m is in the range 5 to 23.

23. A process according to claim 22 in which the said comonomer is selected from the group consisting of n-dodecyl methacrylate, octadecyl methacrylate, hexadecyl-methacrylate, 1H, 1H, 2H, 2H-heptadecafluorodecyl-methacrylate, p-octyl styrene, p-dodecyl styrene and monomethacryloyloxypropyl terminated siloxanes.

24. A process according to claim 23 in which the said comonomer is dodecyl methacrylate.

25. A process according to claim 17 in which the said radical polymerisable monomers include a diluent monomer selected from the group consisting of C$_{1-4}$-alkyl(alk)acrylates, N, N-dialkylamino alkyl(alk)acrylates containing 1 to 4 carbon atoms in each N-alkyl group and 1 to 4 carbon atoms in the alkylene group, C$_{1-4}$ alkyl(alk)acrylamide, hydroxy C$_{1-4}$-alkyl(alk)acrylate, N-vinyl lactam having 5–7 atoms in the lactam ring, styrene, derivatives of styrene having ring substituents selected from C$_{1-4}$ alkyl groups and halogen atoms, polyhydroxyl (alk)acrylates, alkenes, butadiene, maleic anhydride and acrylonitrile.

26. A process according to claim 25 in which the diluent monomer is selected from hydroxy C$_{1-4}$-alkyl(alk)acrylates and polyhydroxyl(alk)acrylates.

27. A process according to claim 17 in which the said radical polymerisable monomers include at least 5% by weight zwitterionic monomer and at least 0.1% by weight monomer having a reactive group.

28. A process according to claim 17 in which the said radical polymerisable monomers include at least 5% by weight zwitterionic monomer and 0.1% to 20% by weight monomer having a reactive group.

29. A process according to claim 25 in which the said radical zwitterionic monomers include at least 5% by weight, at least 0.1% by weight monomer having a reactive group and 5 to 20% by weight diluent monomer.

30. A process according to claim 21 in which the said radical polymerisable monomers include at least 5% by weight zwitterionic monomer, at least 0.1% by weight monomer having a reactive group and 5 to 90% by weight of said comonomer.

31. A process according to claim 17 in which said cross-linkage is by direct reaction of groups Q$^3$ with one another.

32. A process according to claim 17 in which said cross-linkage is by reaction of groups Q$^3$ with a reactive bridging molecule.

33. A polymer according to claim 1 in which X is said group IVC.

34. A process according to claim 17 in which X is said group IVC.

* * * * *